(12) United States Patent
Ogawa et al.

(10) Patent No.: US 7,636,162 B2
(45) Date of Patent: Dec. 22, 2009

(54) MICROCHIP TESTING DEVICE

(75) Inventors: Yoshimasa Ogawa, Himeji (JP);
Kazuyuki Kaneda, Himeji (JP);
Katsutoshi Kabeta, Himeji (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/850,763

(22) Filed: Sep. 6, 2007

(65) Prior Publication Data
US 2008/0062423 A1   Mar. 13, 2008

(30) Foreign Application Priority Data
Sep. 7, 2006   (JP)   ............... 2006-242430

(51) Int. Cl.
G01B 11/00   (2006.01)
G01N 33/48   (2006.01)
G01N 21/00   (2006.01)
G01N 21/75   (2006.01)

(52) U.S. Cl. ............... 356/399; 356/39; 356/432; 356/440; 422/82.09; 436/164

(58) Field of Classification Search ............... None
See application file for complete search history.

(56) References Cited
U.S. PATENT DOCUMENTS

| | | | | |
|---|---|---|---|---|
| 5,876,675 A | * | 3/1999 | Kennedy | ............... 422/99 |
| 6,432,720 B2 | * | 8/2002 | Chow | ............... 436/180 |
| 6,811,668 B1 | * | 11/2004 | Berndt et al. | ............... 204/601 |
| 7,413,707 B2 | * | 8/2008 | Oh et al. | ............... 422/50 |
| 2006/0103848 A1 | | 5/2006 | Nozawa et al. | |
| 2008/0002178 A1 | * | 1/2008 | Ogawa et al. | ............... 356/39 |

* cited by examiner

*Primary Examiner*—Gregory J Toatley, Jr.
*Assistant Examiner*—Gordon J Stock, Jr.
(74) *Attorney, Agent, or Firm*—David S. Safran; Roberts Mlotkowski Safran & Cole, P.C.

(57) ABSTRACT

Microchip testing device having a chip holder that can be exactly positioned and from which adhered sample liquid can be removed easily. The microchip testing device has a chip holder, with a cover and a box area, mounted on a measurement stage, a microchip that has an optical measurement chamber is housed in the chip holder, a light source that radiates light on the optical measurement chamber of the microchip, a detector that receives light that has passed through the optical measurement chamber, and a controller that controls the device. The chip holder has reference planes to position the microchip in two directions perpendicular to the optical axis of the optical measurement chamber and pushers that push the microchip against the reference planes, so that the microchip is positioned within the chip holder by closing the cover of the chip holder.

5 Claims, 22 Drawing Sheets

MICROCHIP TESTING DEVICE

BACKGROUND OF THE INVENTION

1. Field of the Invention

This invention concerns a microchip testing device that has a microchip and that analyzes sample liquids by the light intensity analysis method.

2. Description of Related Art

There has been much attention in recent years to analysis methods that use microchips, called μ-TAS or Lab, on a Chip, with equipment that has been made much smaller, by application of semiconductor miniaturization technology and micromachine production technology, than conventional equipment for chemical analysis and so on. When μ-TAS is used in the medical field, it is possible to lighten the burden on patients by reducing the size of blood and other samples, for example, and it is possible to reduce reagent quantities, and thus, reduce analysis costs. Because of the smaller size of the equipment, there is the additional advantage that analysis can be performed simply.

Absorptiometric analysis using microchips measures the concentration of sample enzymes in blood plasma through a series of operations: (1) sample liquid collected with a painless needle is introduced into the microchip; (2) blood plasma and blood cells are separated by centrifugal processing of the sample liquid within the microchip; (3) the blood plasma and a reagent are mixed evenly to become a measurement sample liquid; (4) the measurement sample liquid is introduced into the optical measurement chamber; and (5) light from a light source is irradiated on the measurement sample liquid introduced into the optical measurement chamber and the attenuation of light of specified wavelengths is measured.

In Japanese Pre-Grant Patent Publication 2006-145309 and corresponding U.S. Patent Application Publication 2006/0103848, for example, there is a description of a microchip testing device in which a measurement sample liquid is introduced into the optical measurement chamber of a microchip, light from a light source is irradiated on the optical measurement chamber, attenuation of light of specified wavelengths is measured by a detector, and the concentration of sample enzymes included in the blood plasma is measured.

FIG. 23 is a schematic representation of an example of a conventional microchip testing device used to analyze sample liquids.

This microchip testing device comprises a chip holder 102, a light source 103, and a detector 104, with a microchip 101 in which an optical measurement chamber 105 has been formed that is housed in the chip holder 102. The light source 103 is located in a position from which it can irradiate the optical measurement chamber 105 with light, and the detector 104 is located in a position from which it can receive light that has passed through the optical measurement chamber 105.

Nevertheless, in the conventional microchip testing device shown in Pre-grant Patent Report 2006-145309 and corresponding U.S. Patent Application Publication 2006/0103848, the construction of the chip holder 102 is not described such that its details can be determined. Further, the diameter of a cross section perpendicular to the optical axis of the optical measurement chamber 105 of the microchip 102 is, for example 1.0 mm$^2$, and with the chip simply accommodated without being positioned within the chip holder 102, it is difficult to radiate the beam accurately. When the beam does not irradiate the optical measurement chamber 105 accurately, the light path of the light transiting the optical measurement chamber 105 is extended slightly and attenuation of the light increases; this can cause erroneous analysis results to be output. Therefore, since absorptiometric analysis requires exact positioning of the microchip 101, it cannot be performed with a microchip 101 that is simply accommodated in the chip holder 102.

Further, there is the possibility that the sample liquid will run over when it is injected into the microchip 101. If the spilled sample liquid adheres to the chip holder 102, it can influence the results from examination of another microchip 101. From the hygienic aspect as well, it is preferable to be able to remove the spilled sample liquid.

SUMMARY OF THE INVENTION

A primary object of this invention is, in view of the problems described above, to provide a microchip testing device having a chip holder that can be exactly positioned and from which adhered sample liquid can be removed easily.

This object is achieved in accordance with the present invention by the following means.

In a first embodiment, the microchip testing device has a chip holder, which comprises a cover and a box area, mounted on a measurement stage, a microchip that has an optical measurement chamber and is housed in the chip holder, a light source that radiates light on the optical measurement chamber of the microchip, a detector that receives light that has passed through the optical measurement chamber, and a controller that controls the equipment, in which the chip holder has reference planes to position the microchip in two directions perpendicular to the optical axis of the optical measurement chamber and pushers that push the microchip against the reference planes, and the microchip is positioned within the chip holder by closing the cover of the chip holder.

In a further development of the first embodiment, there are concave and convex areas on the cover and box area of the chip holder, and the cover and box area engage and separate by means of the interlocking relationship of the convex and concave areas.

By means of the microchip testing device of this invention, the chip holder has reference planes to position the microchip in two directions perpendicular to the optical axis of the optical measurement chamber and pushers that push the microchip against the reference planes, and the microchip is positioned within the chip holder by closing the cover of the chip holder. Therefore, the microchip can be positioned in two directions perpendicular to the optical axis of the optical measurement chamber, so that light from the light source can radiate into the optical measurement chamber accurately, the light that passes the optical measurement chamber can be received, and analysis results can be calculated on the basis of the received light. Further, there are concave areas and convex areas on the cover and box area of the chip holder, and the cover and box area engage and separate by means of the interlocking relationship of the convex and concave areas, so that cleaning can be performed by easily removing the cover of the microchip testing device without using auxiliary tools.

DETAILED DESCRIPTION OF THE INVENTION

A first embodiment of this invention is explained below with reference to FIGS. 1 through 15(*b*5).

Figure 1:
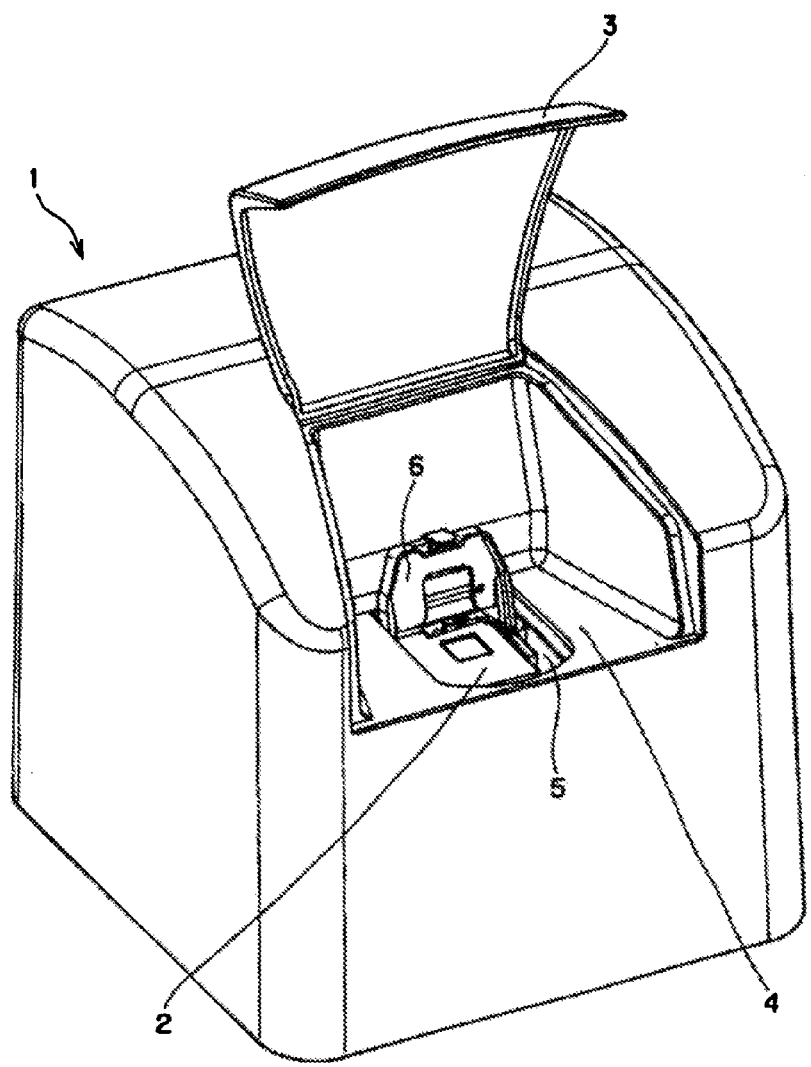
FIG. 1 is a perspective view of the microchip testing device of this invention.

FIG. 1 a perspective view of the microchip testing device of this invention having a rectangular case 1. The case 1 has a case lid 3 so that the microchips 2 can be put in and taken out; it is fixed in place to open and close by means of a hinge, for example. The case lid 3 is opened to enable a microchip 2 to be inserted into the microchip testing device, the microchip is put into the chip holder 5 in the microchip insertion area 4 and then is fixed in place by closing the cover 6, after which the case lid 3 is closed.

FIG. 2(*a*) is a plan view, partially broken away, of a microchip 2 for a single item examination that can be accommodated in the chip holder 5 of the microchip testing device. FIG. 2(*b*) is a cross section taken at line A-A in FIG. 2(*a*), or in other words, a cross section showing the Y direction and the Z direction.

As shown in FIG. 2(*b*), the microchip 2 is formed by joining pieces of opaque resin 7 and transparent resin 8. Also, as shown in FIG. 2(*a*), a fill hole 65 is formed on the upper surface of the microchip 2, a groove that is the channel for the sample liquid is formed on the inside, and an optical measurement chamber 10 that is perhaps 1 mm$^2$ is formed in one place. The sample liquid is introduced into the microchip 2 through the fill hole 65; at a certain stage of the analysis an unillustrated reagent or other material that has been sealed in a certain position is automatically mixed with the sample liquid to become a measurement sample liquid, and the measurement sample liquid is introduced into the optical measurement chamber 10. Analysis is performed using the absorptiometric method or the nephelometric method by measuring light that is passed through the optical measurement chamber 10, or by the fluorometric method using light generated in the optical measurement chamber 10. The light that is incident is not limited to parallel light; it can be convergent light or dispersed light as well. Further, a two-dimensional code 11 is attached to the front of the microchip 2; it contains such information as a serial number, the effective date of the chip, the type of item measured, the position of the optical measurement chamber 10, and the reagent lot for each chip.

Figure 2A:
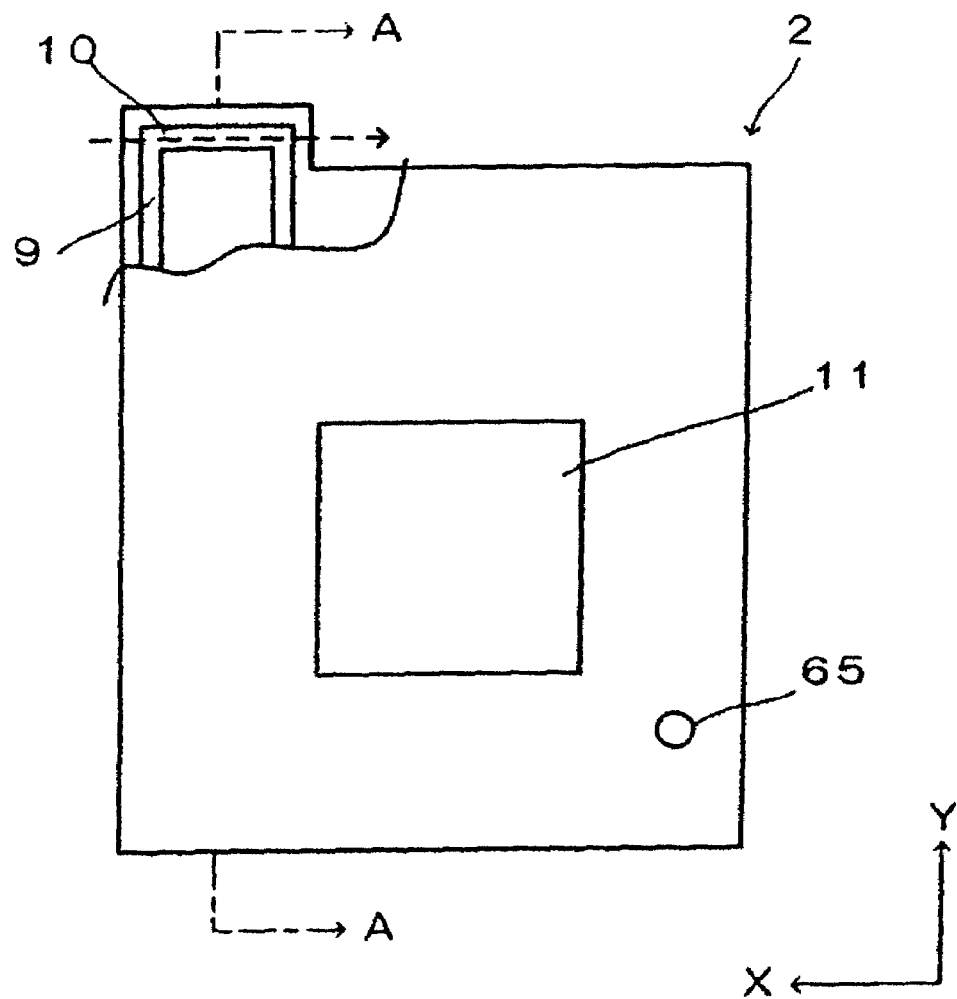
FIGS. 2(a) & 2(b) are, respectively, plan and elevational views of a microchip that are partially in cross section, FIG. 2(b) being a view along line A-A in FIG. 2(a).
Figure 2B:
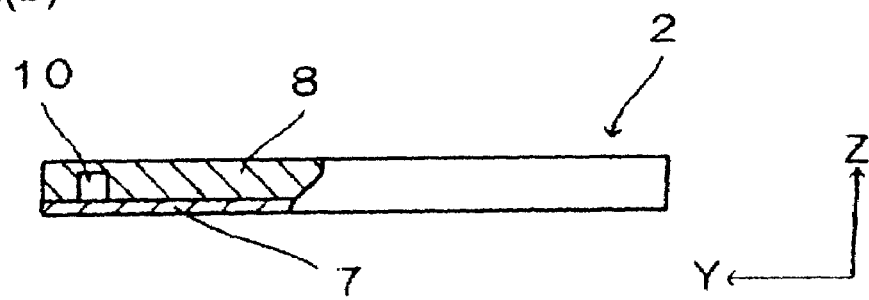
Figure 3:
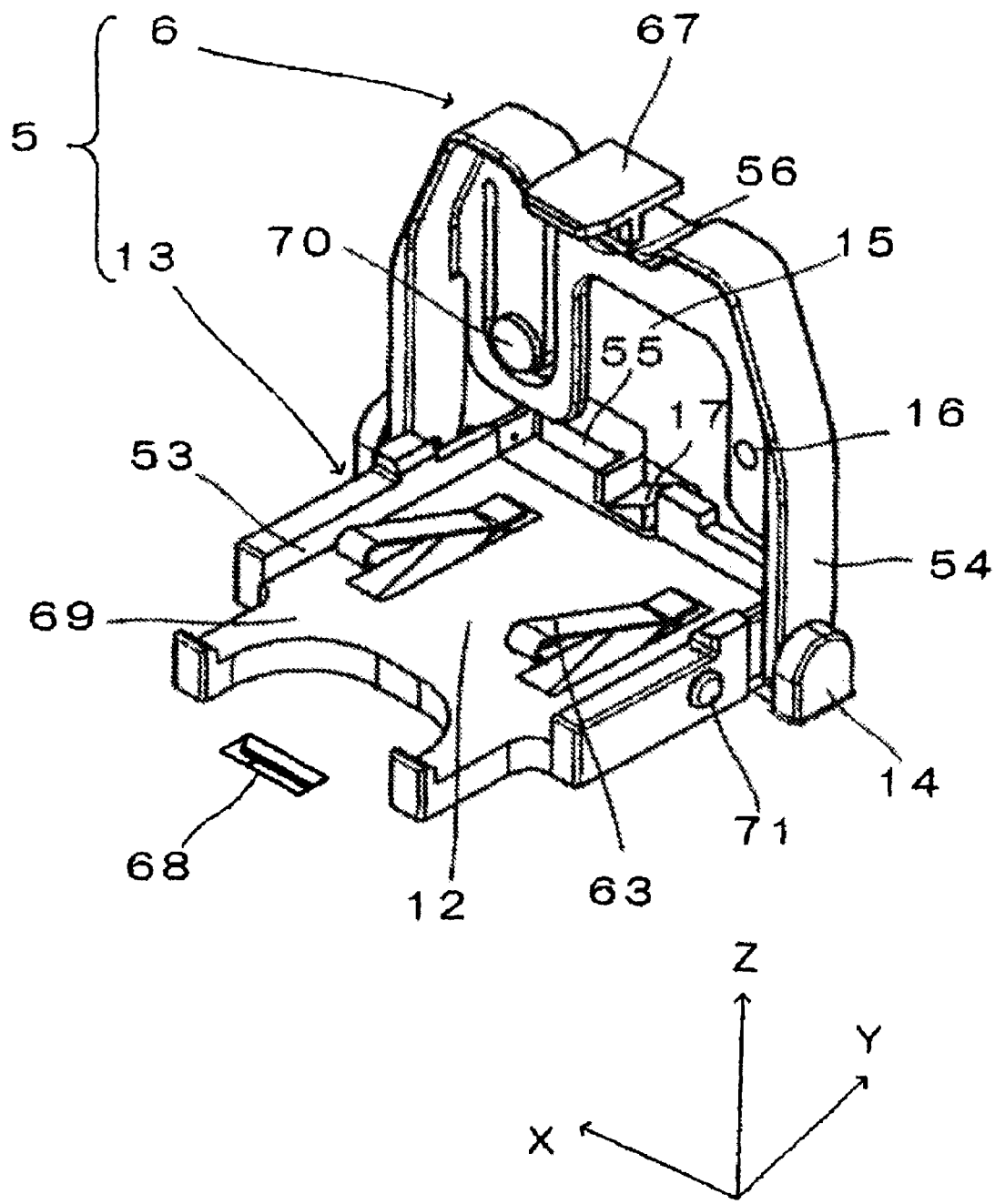
FIG. 3 is a perspective view of the chip holder for the microchip.

FIG. 3 is an external view of the chip holder 5 that accommodates the microchip 2 shown in FIG. 2(*a*).

As shown in the Figure, the chip holder 5 is made of a resin, for example, and comprises a box area 13 that has a chip accommodation space 12 that accommodates the microchip 2, and a cover 6 that positions the microchip 2 in a given location and fixes it in place. There are chip supporters in the box area 13 in which the operator mounts the microchip 2, and fulcrums 14 that support the cover 6. The cover 6 is fixed to the fulcrums 14 by hinges, and has a code reader reading window 15 through which the two-dimensional code attached to the microchip 2 can be read from the outside, and a sample amount sensor reading hole 16 for examining whether the volume of the sample introduced into the microchip 2 is adequate.

So that the cover 6 will not open even when centrifugal force is applied to the microchip 2, a hook 67 on the cover 6 is slipped into a hook catch 68 in the box area 13 and fixed in place. This is because, in the event that blood is used as the sample liquid introduced into the microchip 2, it is necessary to rotate the chip at 3000 rpm for 1 minute, for example, in order to separate the blood into cells and plasma. For that reason, during rotation of the microchip 2, the centrifugal force on the chip holder 5 exceeds 400 G; the cover is fixed in place so that it will not open even under that force.

Further, the chip holder 5 has precision tolerances within ±0.2 mm in the two directions perpendicular to the optical axis of the optical measurement chamber 10, and must be positioned and fixed in place so that the microchip 2 does not move within the chip accommodation space 12. The diameter of a cross section perpendicular to the optical axis of the optical measurement chamber 10 is, for example, 1.0 mm$^2$; that is in order to accurately measure the attenuation of the light at specific wavelengths by radiating light from the unillustrated light source precisely on the optical measurement chamber 10.

The microchip 2 must be easily accommodated in the chip holder 5 so that it can be operated by the operator without trouble. The microchip 2 is supported by the chip supporters 63 so that it lifts up from the chip holder 5 when the cover 6 is opened. When a microchip 2 is inserted, it is enough to place the microchip 2 on the chip supporters 63, and when the microchip 2 is to be removed, the microchip 2 is lifted up from the chip accommodation space 12, and so it is easily removed.

The microchip 2 placed on the chip supporters 63 must be accommodated in the chip accommodation space 12 when the cover 6 is closed. For this reason, the chip accommodation space 12 is formed with an extra margin for the microchip 2. For example, the length of the microchip 2 is 40 mm in the X direction and 50 mm in the Y direction, but the chip accommodation space 12 measures 40.5 mm in the X direction and 50.5 mm in the Y direction.

As such, the microchip 2 has several mm of margin for movement within the chip accommodation space 12 and is not accurately positioned, and so a device to position and fix the microchip 2 in the chip holder 5 is necessary. Therefore, the box area 13 of the chip holder 5 has a Z reference plane 69, a Y reference plane 55, and an X reference plane 54 so that it is possible to position the microchip 2 and fix it in place when the cover 6 is closed by engaging the hook 67 of the cover 6 in the hook catch 68.

Figure 4:
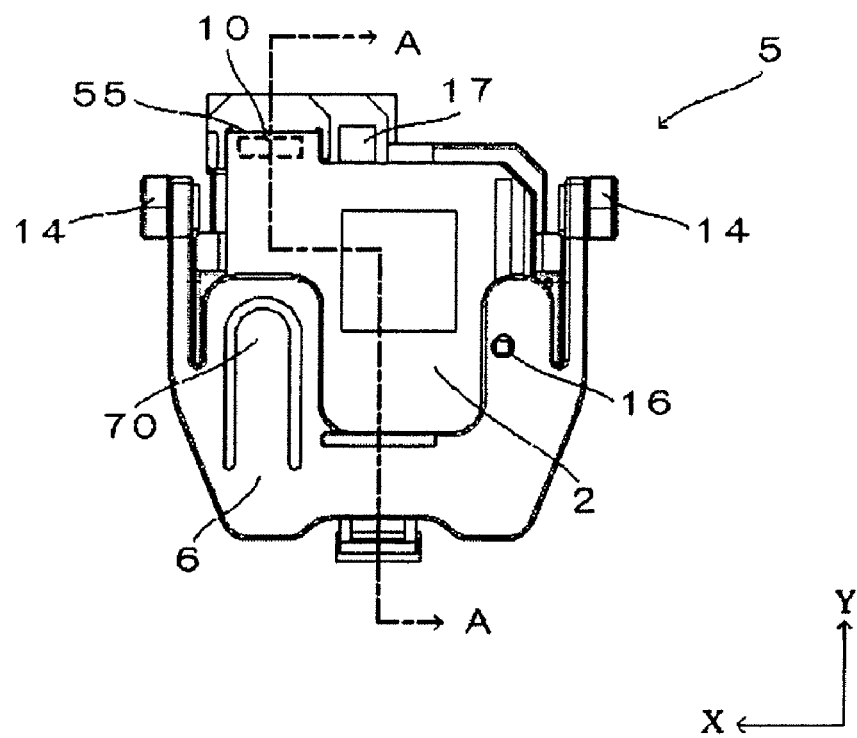
FIGS. 4(*a*) & 4(*b*) are, respectively, plan and elevational views of a microchip that are partially in cross section, FIG. 4(*b*) being a view along line A-A in FIG. 4(*a*).
Figure 4:
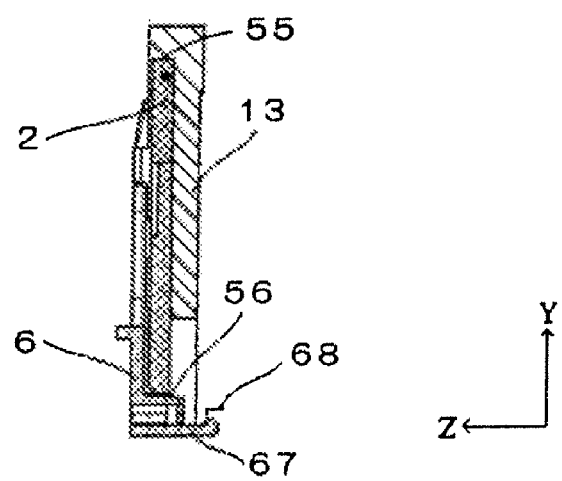
Figure 5:
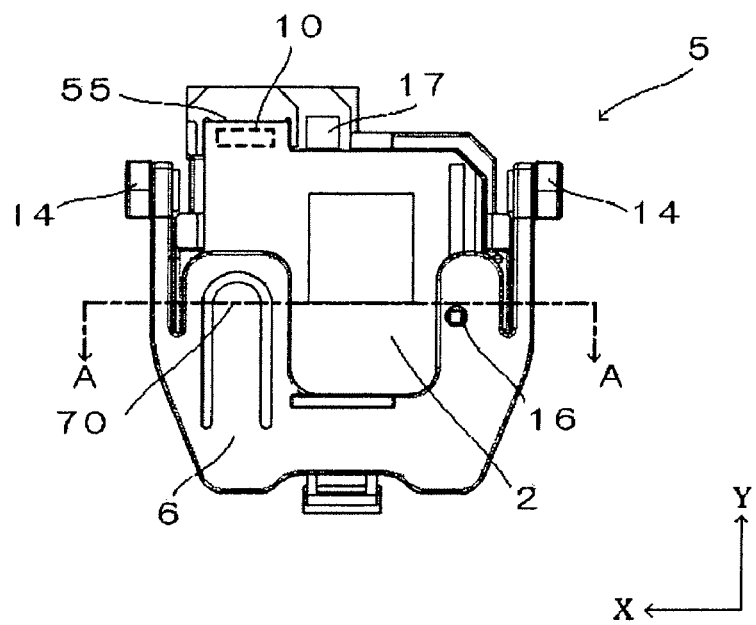
FIGS. 5(*a*) & 5(*b*) are, respectively, plan and elevational views of a microchip that are partially in cross section, FIG. 5(*b*) being a view along line A-A in FIG. 5(*a*).
Figure 5:
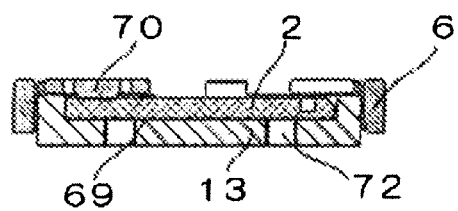
Figure 5:
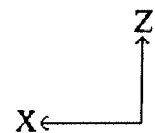
Figure 6:
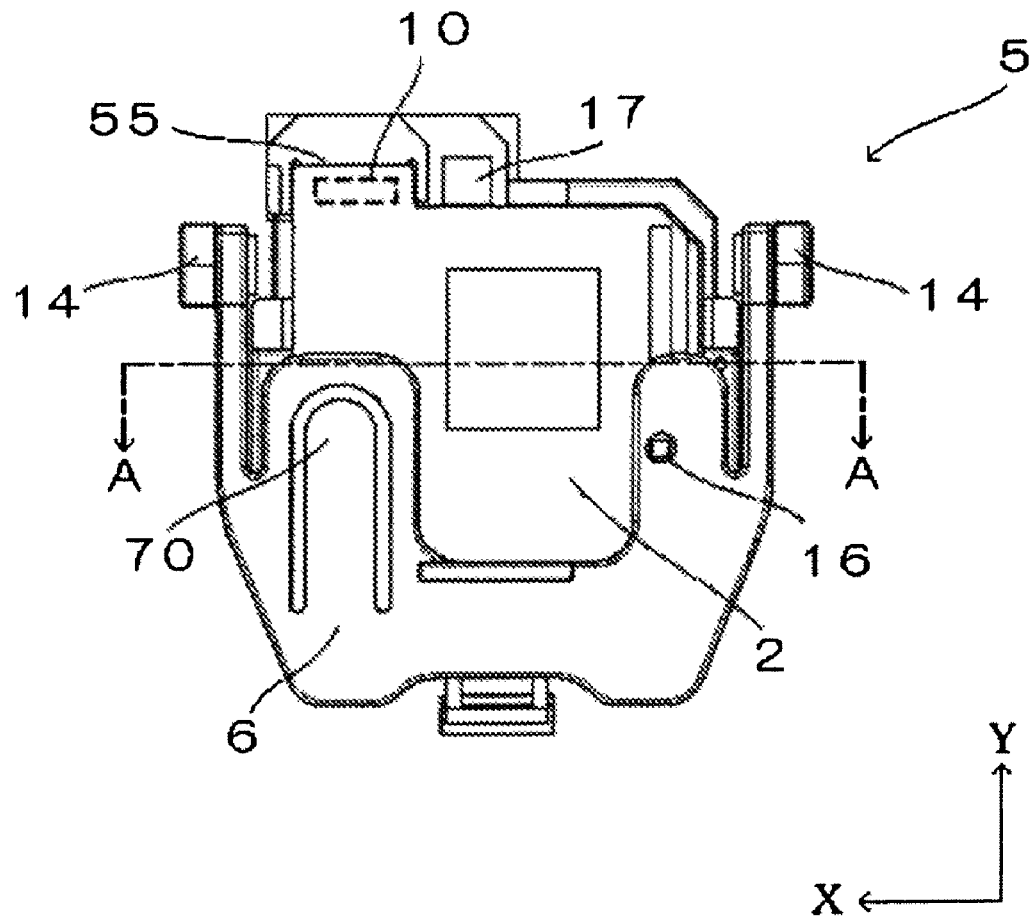
FIGS. 6(*a*) & 6(*b*) are, respectively, plan and elevational views of a microchip that are partially in cross section, FIG. 6(*b*) being a view along line A-A in FIG. 6(*a*).
Figure 6:
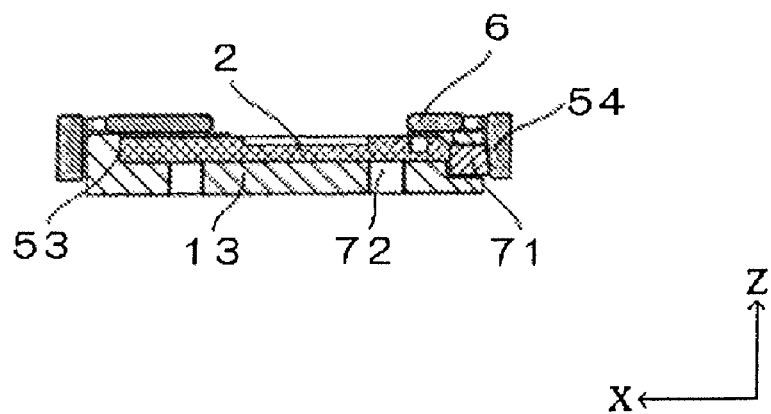

FIGS. 4 through 6 are diagrams to explain the positioning and fixing of the microchip 2 in the chip holder 5 shown in FIG. 3. FIGS. 4(a), 5(a) and 6(a) are top views of the chip holder 5 in which a microchip 2 is housed. FIG. 4(b) is a cross section taken at line A-A of FIG. 4(a), or in other words, a cross section that shows the Y direction and the Z direction. FIG. 5(b) is a cross section taken at line A-A of FIG. 5(a), or in other words, a cross section that shows the X direction and the Z direction. FIG. 6(b) is a cross section taken at line A-A of FIG. 6(a), or in other words, a cross section that shows the X direction and the Z direction.

The positioning mechanism in the Y direction is explained first. As shown in FIG. 4(b), the Y direction pusher 56 operates by having the face of the cover 6 that contacts the microchip 2 having a tapered shape. When the hook 67 of the cover 6 slips into the hook latch 68 of the box area 13 and fixes the microchip 2 in place, at the same time that the hook 67 enters the hook latch 68, the Y direction pusher 56 pushes the microchip 2 in the Y direction and the microchip 2 pushes against the Y reference plane 55. The microchip 2 is placed tightly against the Y reference plane 55, and is positioned with a precision with an error tolerance of ±0.2 mm in the Y direction. At this time, the Y reference plane 55 is not on the Y axis extension line from the Y direction pusher 56, but the rotational force will not work on the microchip 2 because, as explained hereafter, it is positioned and fixed in place in the X direction at the same time.

The positioning mechanism in the Z direction is explained next. As shown in FIG. 5(b), the Y direction pusher 70 operates by means of the fact that the face of the cover 6 that contacts the microchip 2 is thicker than the rest. When the cover 6 closes, the Z direction pusher 70 pushes the microchip 2 against the Z reference plane 69. The chip supporters 63 (not shown in these views) support the microchip 2 when the cover 6 is open, but when the cover 6 is closed, they are housed in supporter accommodation slots 72 by means of pressure from the microchip 2, which is pushed by the Z direction pusher 70.

The microchip 2 is placed tightly against the Z reference plane 69, and is positioned with a precision error tolerance of ±0.2 mm in the Z direction.

In this way, by simply placing the microchip 2 on the chip supporters 63, closing the cover 6 of the chip holder 5, and slipping the hook 67 into the hook latch 68, it is possible to position the microchip 2 in the Y direction and the Z direction—the two directions perpendicular to the optical axis of the light that passes the optical measurement chamber 10.

Now, in the event that the light beam changes direction while passing through the optical measurement chamber 10, it is necessary to position the chip in the two directions perpendicular to the optical axis. For example, in the event that the optical axis changes, within the optical measurement chamber 10, from the X direction to the Y direction, it would be necessary to position the microchip 2 in the Y direction and the Z direction that are perpendicular to the optical axis in the X direction, and in the Z direction and the X direction that are perpendicular to the optical axis in the Y direction, or in other words, it would be necessary to position the microchip 2 in the X direction, the Y direction, and the Z direction. Further, in the event that the optical measurement chamber 10 incorporates a part that reflects the light multiple times, such as an optical waveguide or an optical fiber, the center line of the multiplex reflecting part would be the optical axis.

Further, as stated previously, when the microchip 2 is positioned in the Y direction, it must be positioned to some extent in the X direction as well so that it will not rotate. As shown in FIG. 6(b), an X direction inclusion 71 is held in the box area 13, but is free to move in the X direction. At the same time that the cover 6 closes, an X direction pusher 54 pushes on the X direction inclusion 71, and the X direction inclusion 71 presses the microchip 2 against the X reference plane 53. The microchip 2 is placed tightly against the X reference plane 53, and is positioned with a precision error tolerance within ±0.2 mm in the X direction.

Figure 7A:
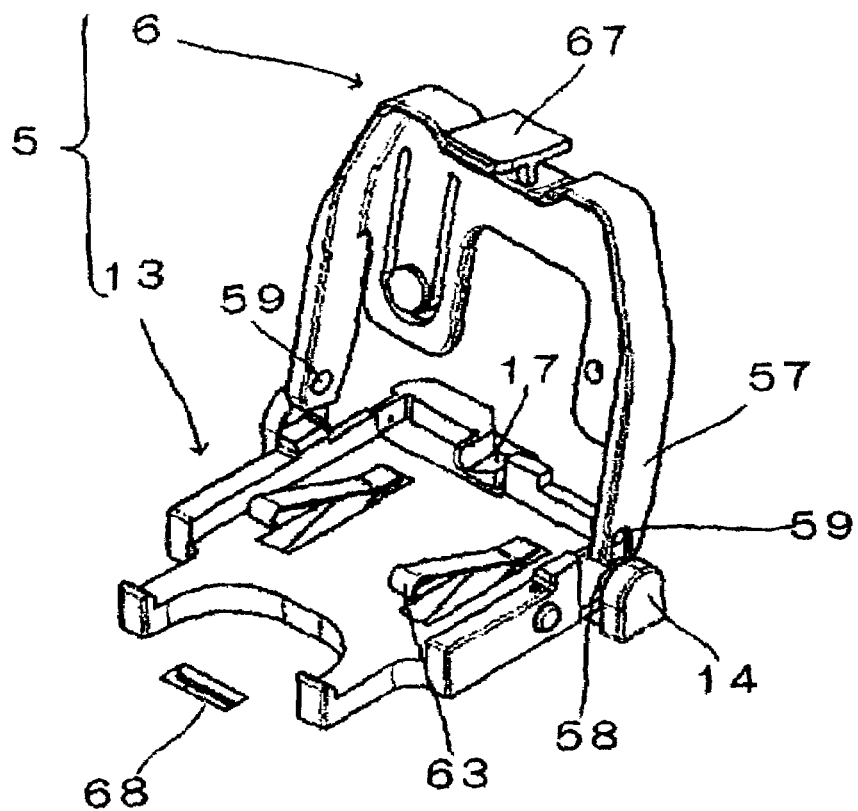
FIG. 7(*a*) is a perspective view of the chip holder and FIG. 7(*b*) show a cross section of the connecting parts of the fulcrum and the cover in engaged and disengaged states.
Figure 7B:
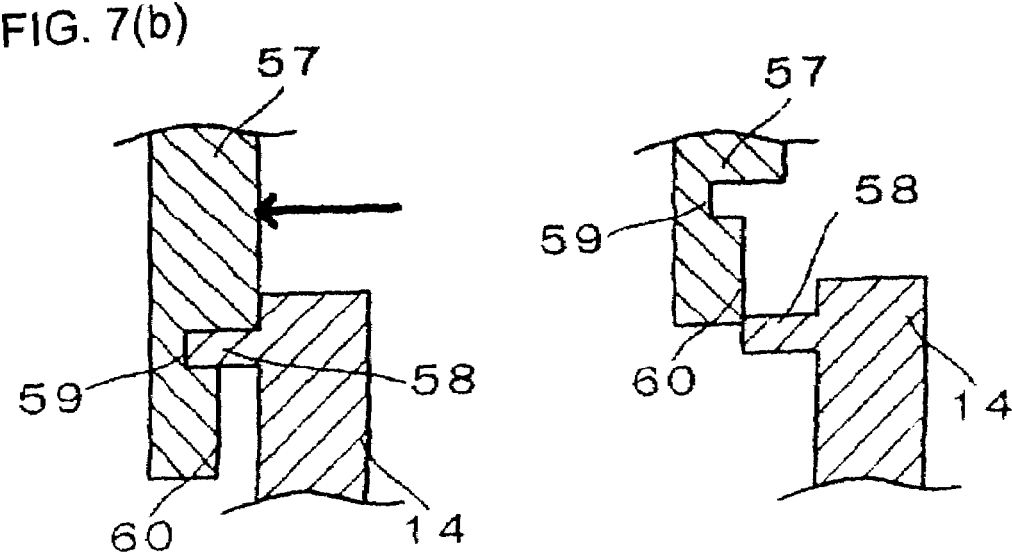

FIG. 7(a) is a diagram to explain that it is possible to remove the cover 6 of the chip holder 5, and FIG. 7(b) is an expanded cross section of the connecting parts of the fulcrum 14 and the cover 6.

In analyses performed by the absorptiometric or other methods using a microchip 2, the sample liquid often has to be only a few μl in volume. However, as shown in FIG. 2, the sample liquid is introduced through a fill hole 65 on the upper surface of the microchip 2, and so it is conceivable that the operator will spill sample liquid around the fill hole 65. Even though a very small amount of sample liquid is spilled, there is the possibility that the sample liquid will adhere to the chip holder cover 6 that contacts the upper surface of the microchip 2. As a result, it is possible that the adhered sample liquid could influence analysis results; its removal is desirable from the hygienic aspect as well. Therefore, it has been made possible to remove the cover 6, as shown in FIG. 7(b) to clean it.

The removal mechanism of the cover 6 is now explained. The operator pushes the side arms 57 of the cover 6 inward in the X direction on both sides and pulls up, by which means the cover 6 can be removed from the box area 13. As shown in FIG. 7(b), when the side arm 57 is pushed in the direction of the arrow, a convex part 58, which functions as an axis of rotation of the fulcrum 14, comes out of a concave part 59 on the side arm 57, and if the cover 6 is pulled upwards while held in this state, the convex part 58 slides in a shallow groove 60 so that the cover 6 can be removed from the fulcrum 14. This operation can be reversed when the cover 6 is fastened to the box area 13. Because of the way that the concave parts 59 on the cover 6 and convex parts 58 on the box area 13 of the chip holder 5 are fitted together, the cover 6 and the box area 13 can be separated or put together by simply pressing the side arms 57 of the cover 6 inward in the X direction and pulling up or pressing the side arms 57 inward in the X direction and pushing down. Thus, it is possible to remove the cover 6 from the microchip testing device and clean it easily, without the use of auxiliary tools, such as a screwdriver or wrench, for example.

Figure 8:
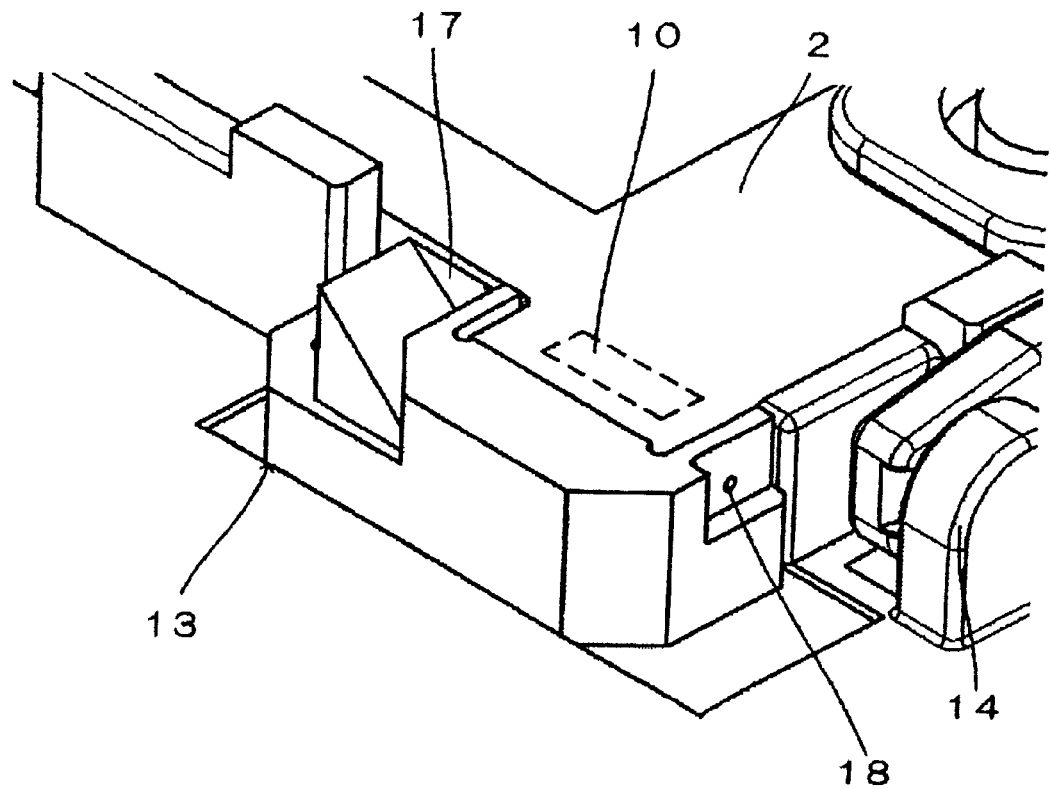
FIG. 8 is an enlarged perspective view of a portion of the chip holder in the optical measurement chamber.

FIG. 8 is an enlarged view of a portion of the chip holder 5 shown in FIG. 3, and is used to explain the transit of light through the optical measurement chamber 10 of a microchip 2 accommodated in the chip holder 5.

As shown in the Figure, an aperture 18 is formed in the side of the chip holder 5, and light from an unillustrated light source radiates through the aperture 18 into the optical measurement chamber 10 of the microchip 2. The aperture 18 has a shape corresponding to the cross section of the optical measurement chamber 10 of the microchip 2, for example, a hole with a diameter of 0.6 mm; it has a shielding function so that excess light does not enter the optical measurement chamber 10. The light that radiates through the aperture 18 passes the optical measurement chamber 10 and emerges from a light transit hole that is not shown in this Figure. The light that emerges is reflected by a mirror 17 and received by a detector (not shown in this Figure).

Figure 9:
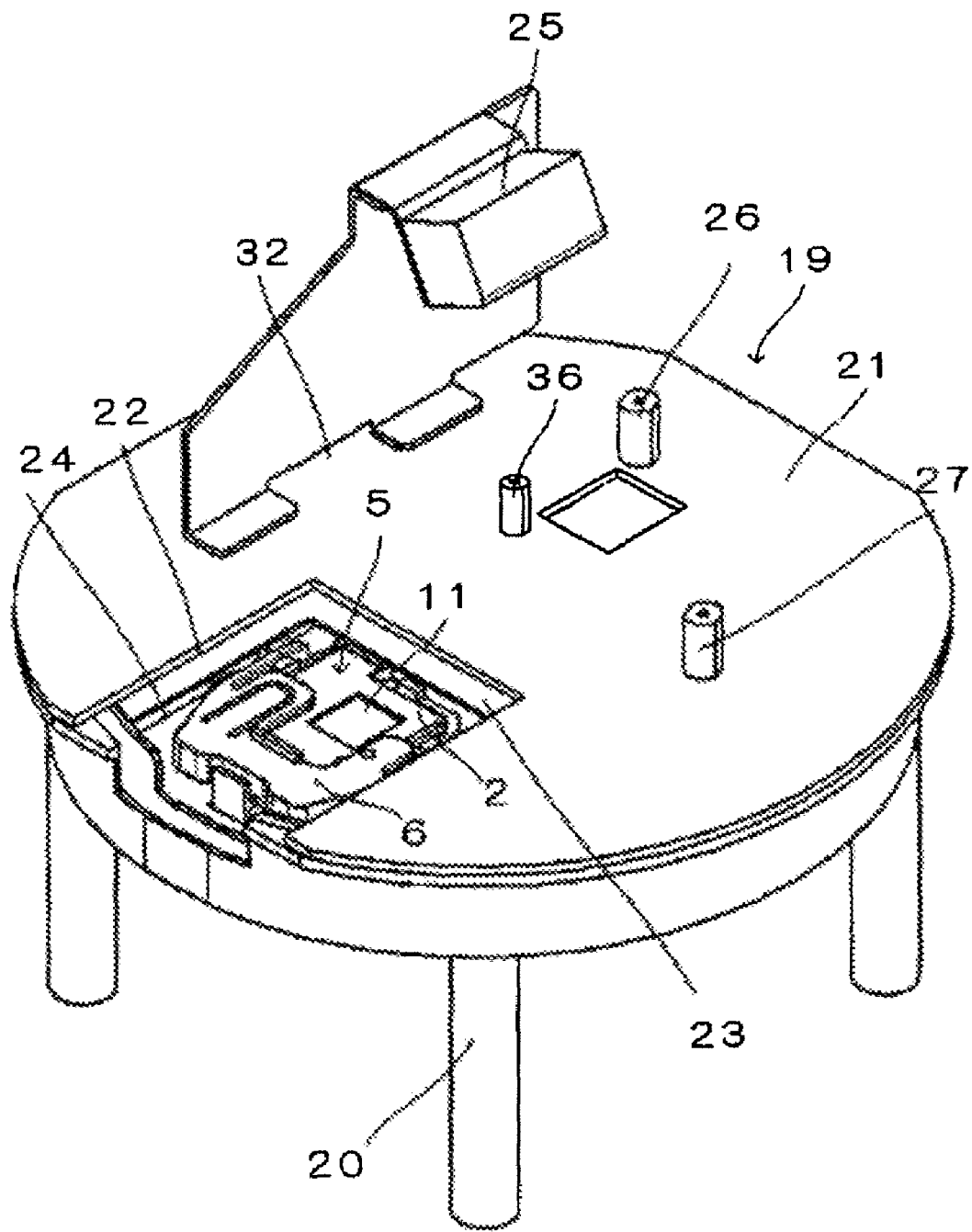
FIG. 9 is a perspective view of measurement chamber located within the case.

FIG. 9 is a perspective view of a measurement chamber 19 located inside the case 1 of the microchip testing device.

As shown in the Figure, the measurement chamber 19 is in the shape of a hollow disk, and is supported by, for example, four legs 20. On the upper face 21 of the measurement chamber 19 is a measurement chamber chip insertion window 22 in a position corresponding to the microchip insertion area 4 of the case 1 shown in FIG. 1. Inside the measurement chamber 19, moreover, there is a measurement stage 23 in the shape of a hollow disk, and on the upper face of the measurement stage 23 is a stage chip insertion window 24 in a position corresponding to the microchip insertion area 4 of the case 1. By this means, it is possible to operate the chip holder 5 directly from the microchip insertion area 4 when the case lid 3 (shown in FIG. 1) is open.

Further, a detector 36 that receives the light that is reflected by the mirror 17 after passing through the optical measurement chamber 10, a code reader 25 that reads the two-dimensional code 11 attached on the microchip 2, a sample amount sensor 26 that measures the volume of the sample introduced into the microchip 2, and a reflection sensor 27 that detects the orientation of the microchip 2 are installed on the upper surface of the measurement chamber 19. The code reader 25, the sample amount sensor 26, and the reflection sensor 27 can be attached in any position desired, but in order to avoid such things as stray light that enters the measurement chamber 22 through the measurement chamber chip insertion window 22, they are preferably positioned away from the measurement chamber chip insertion window 22. Now, as long as the code reader 25, the sample amount sensor 26, and the reflection sensor 27 are placed in positions that correspond to the specified position of the microchip 2, it is possible to make two or three measurements simultaneously.

The detector 36 receives the light that is reflected by the mirror 17 after passing through the optical measurement chamber 10. A light intensity signal is output on the basis of the amount of light received by the detector 36, and the examination results are calculated from the signal. The detector 36 comprises a photoreceptor element, which can be, for example, a silicon photodiode. The silicon photodiode is a photoreceptor element having sensitivity to light in the wavelength region from 300 to 1100 nm. In other words, a light intensity signal based on the amount of light received by the detector 36 is output, the attenuation of light at a specified wavelength is measured, and the concentration of the detection sample component in the measurement sample liquid in the optical measurement chamber 10 is calculated.

The code reader 25 has the function of reading in the two-dimensional code 11 attached on the microchip 2, it is located somewhat apart from the measurement chamber 19 for such reasons as matching the focal point of the lens in order to read the two-dimensional code 11 as an image. The speed of revolution applied to the microchip 2, the revolution period and the centrifugal direction are decided on the basis of the information recorded in the two-dimensional code 11.

The sample amount sensor 26 has the function of confirming whether enough sample liquid has been introduced into the microchip 2; the sample amount sensor 26 emits light of a wavelength that is easily absorbed by the sample liquid—the 550 nm region, for example—toward the channel in the microchip 2 and measures the intensity of the reflected light. If enough sample liquid has been introduced into the microchip 2, that light will be absorbed by the sample liquid and hardly any reflected light will be detected by the sample amount sensor 26. If not enough sample liquid has been introduced into the microchip 2, light will be reflected from the bottom face of the channel in the microchip 2, and the reflected light will be detected by the sample amount sensor 26 with hardly any attenuation. It is possible, by this means, to determine whether enough sample liquid has been introduced into the microchip 2 on the basis of the intensity of the light received by the sample amount sensor 26.

The reflection sensor 27 has the function of detecting the orientation of the microchip 2; When processing of the microchip 2 has stopped suddenly because of a power loss or because something like vibration of the microchip testing device has activated the safety stop mechanism, the processing can be restarted after the orientation of the microchip 2 is confirmed by the reflection sensor 27.

Figure 10:
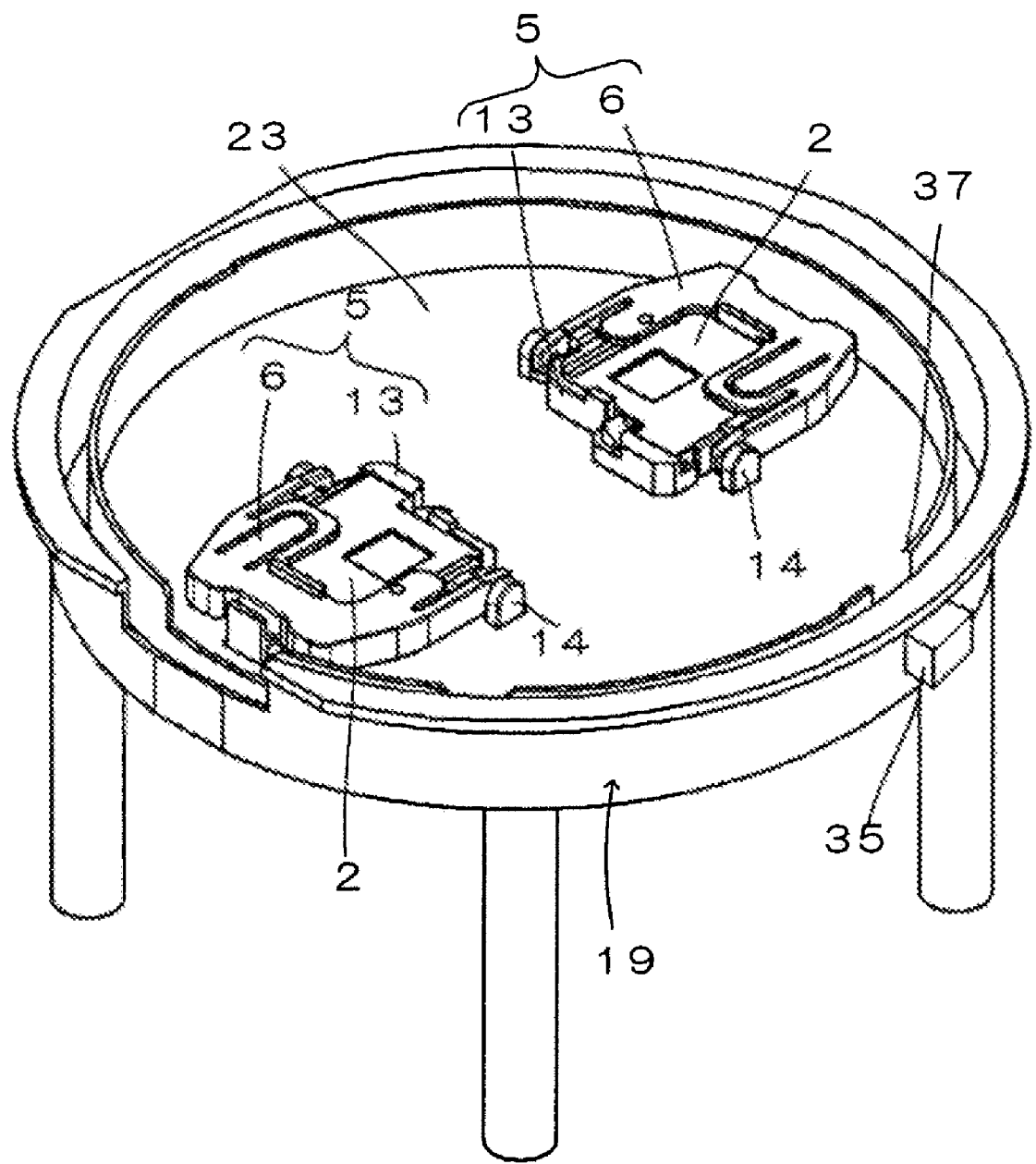
FIG. 10 is a perspective view showing the internal structure of the measurement chamber.

FIG. 10 is a perspective view that shows the internal structure of the measurement chamber 19 shown in FIG. 9, following removal of the upper face of the measurement chamber 19 and the upper face of the measurement stage 23.

As shown in the FIG. 10, the microchips 2 are arranged symmetrically with respect to the center of the measurement stage 23. The box area of the chip holder 5 is formed as a single unit with the measurement stage 23, and the cover 6 is fixed by hinges to the fulcrums 14 that project from the measurement stage 23. The measurement stage 23 is rotated counter-clockwise by an unillustrated rotary drive source.

A light source 35 is attached to the side of the measurement chamber 19. The light source 35 is located so that when the microchip 2 is in a specified position, the light emitted from the light source 35 passes through the aperture 18 of the chip holder 5 as shown in FIG. 8, passes the optical measurement chamber 10 of the microchip 2, is reflected by the mirror 17 of the chip holder 5, and is received by the detector 36. Further, there is a light source slot 37 in the side of the measurement stage 23, in a position that corresponds to the light source 35, so that the light emitted by the light source 35 is not blocked.

Such things as a xenon lamp, an ultra high-pressure mercury lamp of the kind suitable for use as a projector light source, a short-arc type metal halide lamp, an LED, or an LD can be used as the light source 35. Now, use of a power-saving 20 to 75 W short-arc type xenon lamp is preferable because it provides great light intensity and is easily adapted as a point light source, because it has a continuous spectrum in the broad wavelength region from 250 to 1400 nm, and particularly, because it has a stable emission spectrum without bright lines in the wavelength region that is often used in absorptiometric analysis (specifically, the wavelength region from 300 to 800 nm).

In this way, the box area 13 has a Y reference plane 55 and a Z reference plane 69 (see FIGS. 3 and 5(a) & 5(b), for example) that position the microchip 2 in the two directions perpendicular to the optical axis of the optical measurement chamber 10 of the chip holder 5, so that the microchip 2 can be positioned within the chip holder 5 by closing the cover 6, on which there are a Y direction pusher 56 and a Z direction pusher 70 that push the microchip 2 against their respective reference plane. By this means, the microchip 2 can be positioned with respect to the two directions perpendicular to the optical axis of the optical measurement chamber 10, and so the light from the light source 35 can accurately enter the optical measurement chamber 10, the light that passes the optical measurement chamber 10 can be received, and the analysis results can be calculated on the basis of the amount of light received.

Figure 11:
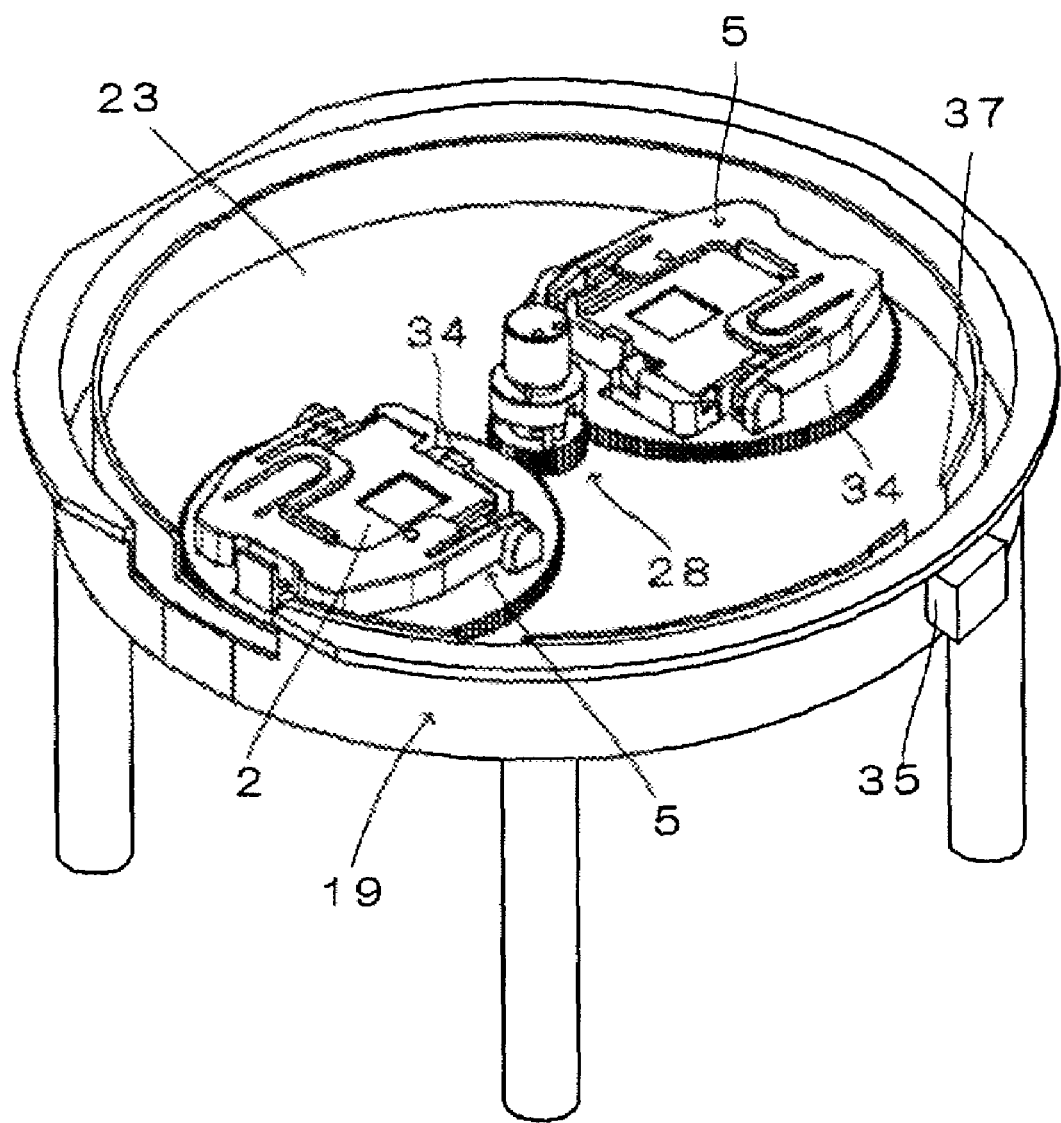
FIG. 11 is a perspective view showing the internal structure of the measurement chamber with a centrifugal direction-switching mechanism.

FIG. 11 is a perspective view showing the internal structure of the measurement chamber 19 with a centrifugal direction-switching mechanism 28 installed.

There may be a necessity of moving the sample liquid within the microchip 2 in a rather complicated way by automatically switching the centrifugal direction applied to the microchip 2. In such a case, a centrifugal direction-switching mechanism 28 is installed in the center of the measurement stage 23 as shown in the Figure, and microchips 2 are housed in chip holders 5 that are arranged symmetrically on the centrifugal direction-switching mechanism 28. The chip holders 5 are installed atop planetary gears 34 that are formed with teeth on their peripheries.

Now, the main shaft rotary unit and the planetary rotary units have, for example, toothed gears that engage tooth on tooth or friction rollers that engage rubber on rubber. The explanation that follows deals with the use of a toothed main shaft gear 44 and planetary gears 34 that engage tooth on tooth, but of course it is possible to switch the centrifugal direction in the same way using such things as rollers. Further, it is possible to install the box area 13 of the chip holder 5 and the planetary gear 34 with teeth formed on the periphery as separate units.

Figure 12:
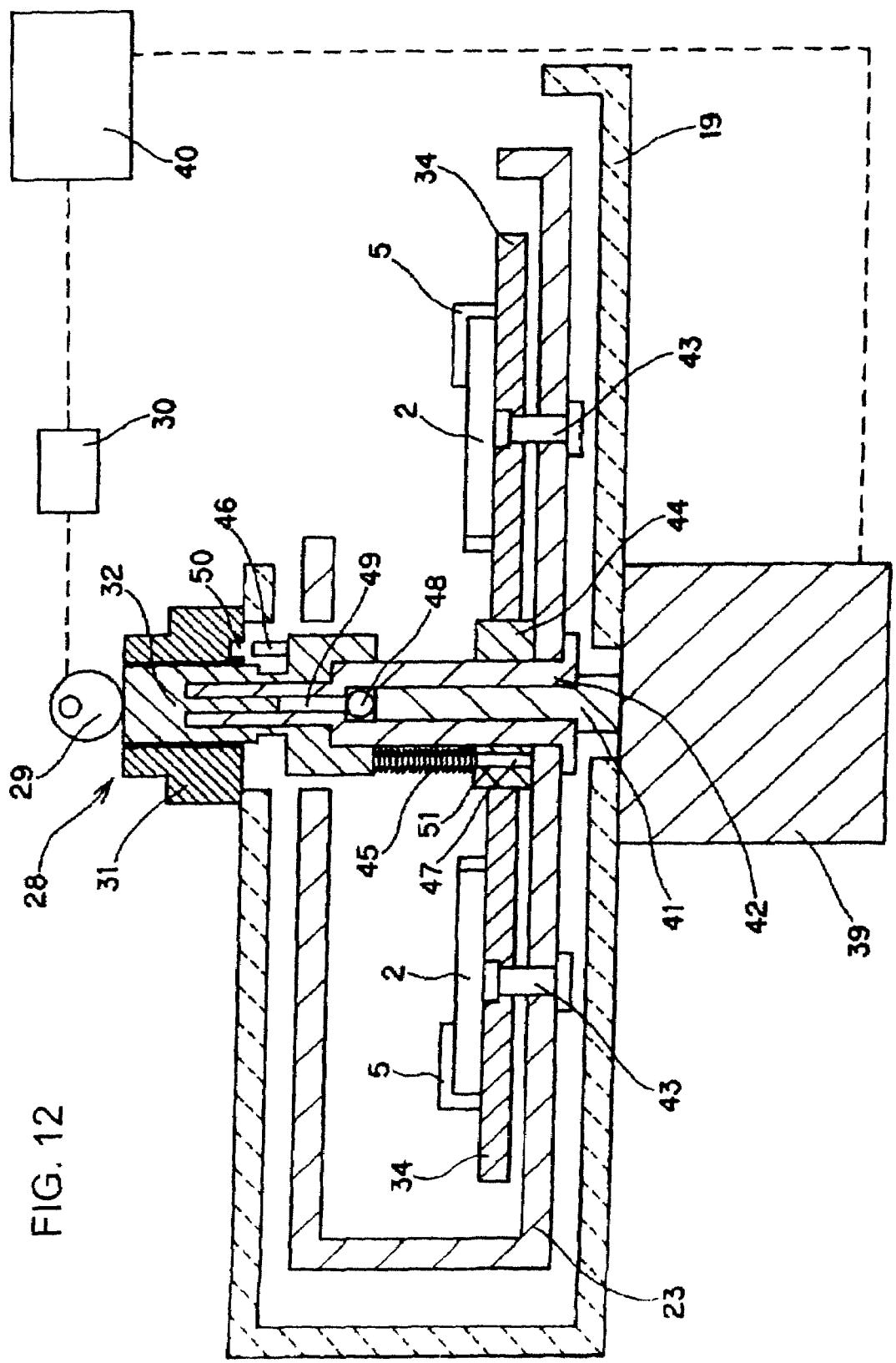
FIG. 12 is a cross-sectional showing the internal structure within the case of the microchip testing device.

FIG. 12 is a cross section of the internal mechanism within the microchip testing device in which the centrifugal direction-switching mechanism 28 has been installed. As shown in the Figure, a rotary drive source 39 is fixed to the measurement chamber 19, and is controlled by a controller 40. The centrifugal direction-switching mechanism 28 is also controlled by the controller 40 to drive the direction-switching motor 30. A rotary shaft 41 extends from the top center of the rotary drive source 39, and a main shaft 42 is fixed to the rotary shaft 41, by a thread fastening, for example, so as to cover the rotary shaft 41. By this means, the main shaft 42 is rotated by the rotary drive source 39. Further, the measurement stage 23 is connected to the main shaft 42; it is fixed to the main shaft 42 by a thread fastening, for example. Therefore, the rotary shaft 41, the main shaft 42, and the measurement stage 23 are imparted rotary movement from the rotary drive source 39, and rotate as a unit. The planetary gears 34 maintain a clearance of 0.2 mm, for example, from the measurement stage 23, and are attached by a thread fastening so that they are free to rotate on planetary main shafts 43 that are fixed to the measurement stage 23.

The rotary drive source 39 comprises a DC motor and encoder; it is controlled by the controller 40, and can stop the measurement stage 23 at a specified angle with a precision of 0.01° to 0.1°. In other words, the microchip 2 can be positioned, rotated, or stopped with a precision of 0.01 to 0.1 mm in the circumferential direction.

The encoder radiates a light through slits on a rotary disk on the circumference of which there are numerous parallel optical slits, and measures the angle of rotation and the speed of rotation from the controller 40 by detecting that light. Based on the measured values, the controller 40 sends ON/OFF signals to the DC motor, by means of which the rotary drive source 39 is rotated at the desired speed or stopped at the desired angle. If, when rotation stops, the encoder measures slight movement from the stop position, the controller 40 can attain the proper stop position by rotating the DC motor in the reverse direction. Now, it is also possible to use a stepping motor as the rotary drive source 39. However, stepping motors have poor rotational efficiency, and so the design must give consideration to heat generated when the rotary speed is raised and the low torque at high rotary speeds.

The main shaft gear 44 that engages the planetary gears 34 is mounted freely fitting on the main shaft 42, and the main shaft 42 and the main shaft gear 44 can each rotate independently. Further, a vertically moving shaft 32 of the centrifugal direction-switching mechanism 28 is connected to the top of the main shaft 42. The centrifugal direction-switching mechanism 28 comprises an eccentric cam 29, a sliding bearing 31, the vertically moving shaft 32, a spring 45, a top engaging pin 46, a bottom engaging pin 47, a main shaft connecting pin 48, and the direction-switching motor 30. The vertically moving shaft 32 has its center shaft inserted into the central slot 49 of the main shaft 42; it matches the main shaft 42 and the central axis of the centrifugal direction-switching mechanism 28 with good precision. Further, the vertically moving shaft 32 has a top engaging pin 46 and a bottom engaging pin 47. The sliding bearing 31 has a top engaging pin slot 50 into which the top engaging pin 46 is inserted, and the main shaft gear 44 has a bottom engaging pin slot 51 into which the bottom engaging pin 47 is inserted. Because the bottom engaging pin 47 is inserted in the bottom engaging pin slot 51 by way of the spring 45, there is always an upward force working on the vertically moving shaft 32. However, the upper face of the vertically moving shaft 32 is in contact with the eccentric cam 29, and so there is pressure that works against upward movement of the vertically moving shaft 32.

Figures 13A, 13B:
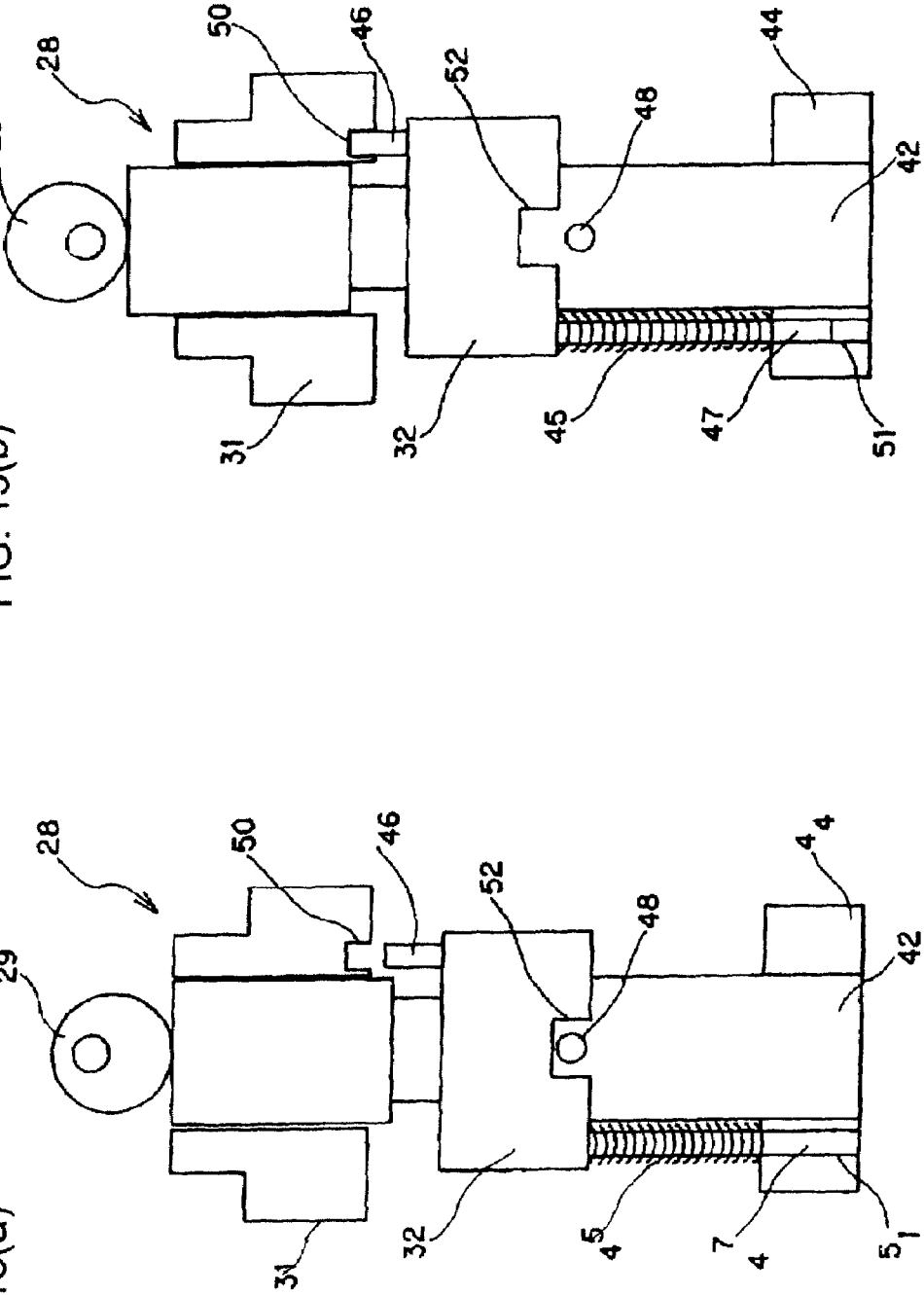
FIGS. 13(*a*) & 13(*b*) are diagrams for explaining the operation of the centrifugal direction-switching mechanism of the microchip testing device.
Figure 14:
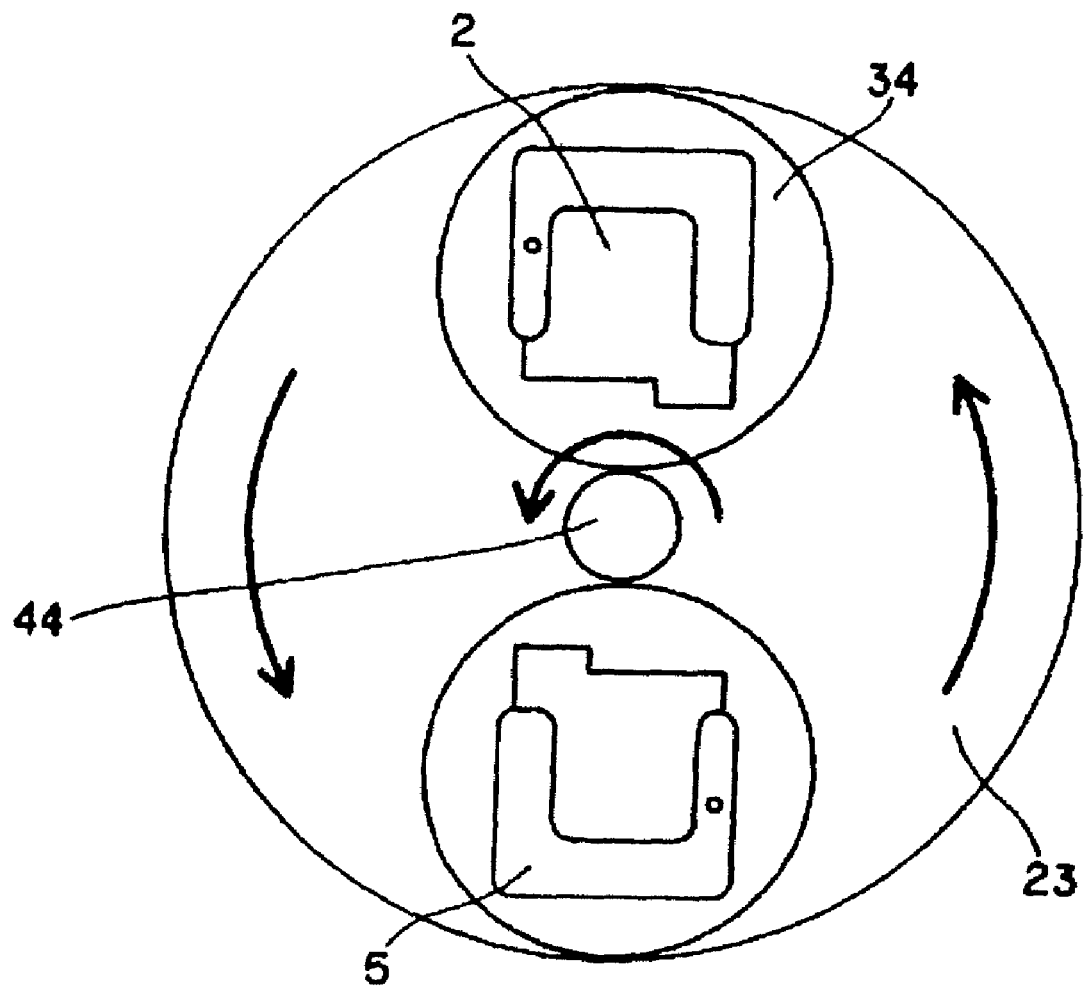
FIG. 14 is an diagram for explaining the operational relationship of the measurement stage, main-shaft gear, and planetary gear of the microchip testing device in the centrifugation mode.
Figure 15:
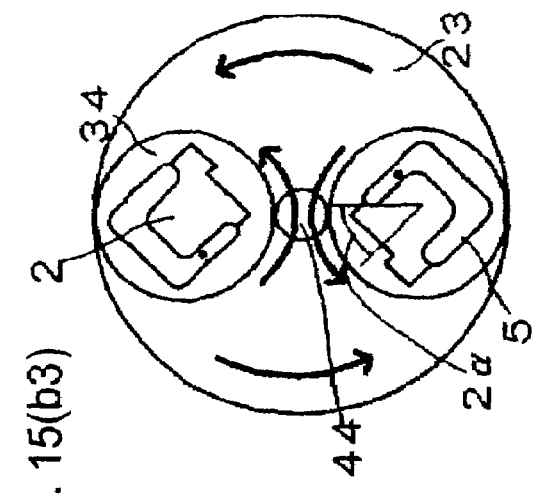
FIGS. 15(*b*1)-15(*b*5) are diagrams for explaining the operational relationship of the measurement stage, main-shaft gear, and planetary gear of the microchip testing device in the centrifugal direction-switching mode.
Figure 15:
Figure 15:
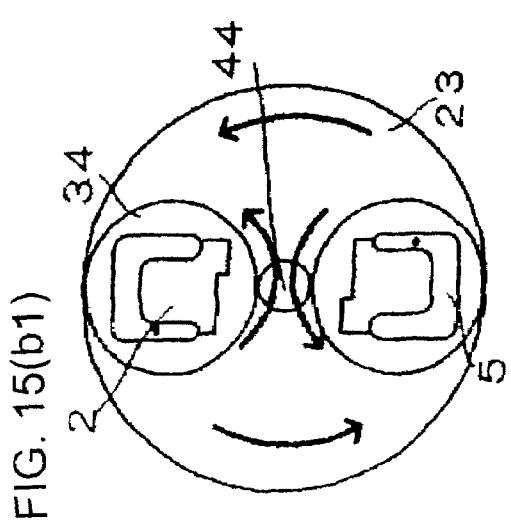
Figure 15:
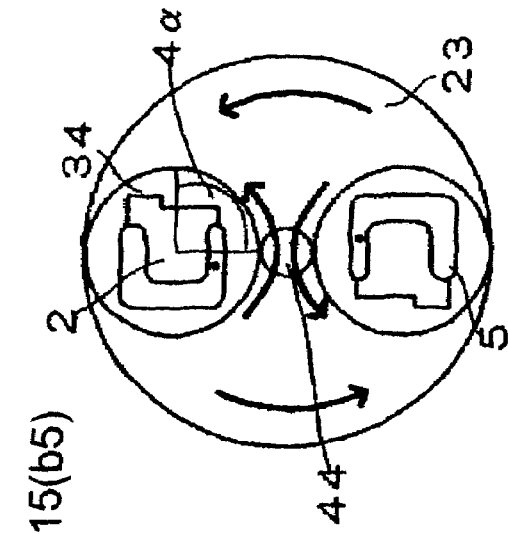
Figure 15:
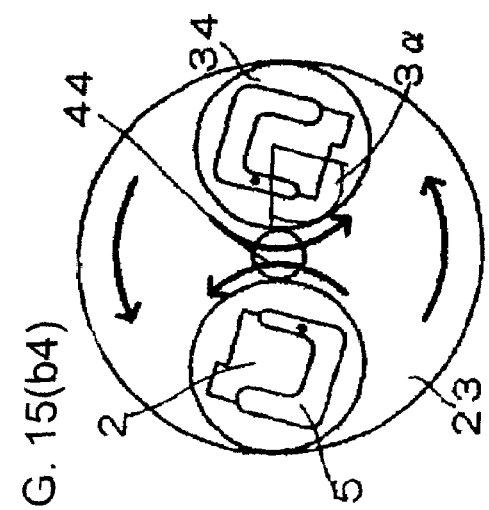

FIGS. 13(a) & 13(b) are Figures for explaining the operation of the centrifugal direction-switching mechanism 28 of the microchip testing device; FIG. 13(a) shows the state of the centrifugation mode with the vertically moving shaft 32 moved downward, and FIG. 13(b) shows the state of the centrifugal direction-switching mode with the vertically moving shaft 32 moved upward. FIG. 14 and FIGS. 15(b1) to 15(b5) are diagrams to explain the operational relationship of the measurement stage 23, the main shaft gear 44, and the planetary gears 34 in the microchip testing device. FIG. 14 shows the centrifugation mode, and FIGS. 15(b1) to 15(b5) show the centrifugal direction-switching mode.

When the vertically moving shaft 32 is downward in the centrifugation state, as shown in FIG. 13(a), the main shaft connecting pin 48 that protrudes from the main shaft 42 engages with the rotation restricting slot 52 of the vertically moving shaft 32 so that the vertically moving shaft 32 is controlled by the main shaft 42 and rotates together with the main shaft 42. Further, the movement of the main shaft gear 44 is restricted by the bottom engaging pin 47, so that it rotates together with the main shaft 42. Therefore, as shown in FIG. 14, the main shaft gear 44 rotates at the same speed of rotation as the measurement stage 23, so that no relative motion is produced in the planetary gears 34 that are fixed to the measurement stage 23, so that revolution with the main shaft 42 as a center point is possible without rotation of the planetary gears 34. In other words, when the vertically moving shaft 32 is downward, the microchip 2 revolves around the main shaft 42 and centrifugal force acts on it, and so it is in the centrifugation mode.

When the controller 40 drives the direction-switching motor 30 and the eccentric cam 29 is rotated 180°, the vertically moving shaft 32 moves upward because of the upward force of the spring 45. As shown in FIG. 13(b), the vertically moving shaft 32 is upward, the rotation restricting slot 52 of the vertically moving shaft 32 comes off the main shaft connecting pin 48, the top engaging pin 46 is inserted in the top engaging pin slot 50 of the sliding bearing 31, and movement of the vertically moving shaft 32 is restricted by the sliding bearing 31 that is fixed to the measurement chamber 19, so that the vertically moving shaft 32 is fixed and does not rotate. Further, movement of the main shaft gear 44 is restricted by the bottom engaging pin 47, so it is connected to the measurement stage 19, fixed in place, and does not rotate. Now, the main shaft gear 44 here is connected to the measurement chamber 19 and fixed in place so it does not rotate, but of course could be connected to parts that do not rotate other than the measurement chamber 19, as long as the main shaft gear 44 does not rotate.

The movement of the microchip 2 when the vertically moving shaft 32 is upward as shown in FIG. 13(b) is explained with reference to FIGS. 15(b1) through 15(b5). FIG. 15(b1) shows the state when the vertically moving shaft 32 is upward. The main shaft gear 44 is fixed and does not rotate, but the planetary gears 34 are fixed to the measurement stage 23 and are able to rotate, and so they rotate along with the measurement stage 23. Because the planetary gears 34 are engaged with the main shaft gear 44, when the measurement stage 23 rotates, the planetary gears 34 also rotate while engaging the main shaft gear 44. In other words, the planetary gears 34 have a planetary motion in which they revolve around the main shaft 42 while rotating on the planetary main shafts 43.

FIG. 15(b2) shows the state when the measurement stage 23 has rotated 90° from the state shown in FIG. 15(b1). The planetary gears 34 have revolved 90° around the main shaft 42 along with the rotation of the measurement stage 23. Further, because the planetary gears 34 are engaged with the main shaft gear 44 and are able to turn, the microchips 2 have also rotated $\alpha°$. This a is a number determined by the relationship between the number of teeth on each planetary gear 34 and the number of teeth on the main shaft gear 44. For example, if the number of teeth on each planetary gear 34 is four times the number of teeth on the main shaft gear 34, $\alpha$ is 22.5. FIG. 15(b3) shows the state when the measurement stage 23 has rotated 180° from the state shown in FIG. 15(b1). The planetary gears 34 have revolved 180° around the main shaft 42 along with the rotation of the measurement stage 23. Because the planetary gears 34 are engaged with the main shaft gear 44 and are able to turn, the microchips 2 have also rotated $2\alpha°$.

FIG. 15(b4) shows the state when the measurement stage 23 has rotated 270° from the state shown in FIG. 15(b1). The planetary gears 34 have revolved 270° around the main shaft 42 along with the rotation of the measurement stage 23. Because the planetary gears 34 are engaged with the main shaft gear 44 and are able to turn, the microchips 2 have also rotated $3\alpha°$. FIG. 15(b5) shows the state when the measurement stage 23 has rotated 360° from the state shown in FIG. 15(b1). The planetary gears 34 have revolved 360° around the main shaft 42 along with the rotation of the measurement stage 23. Because the planetary gears 34 are engaged with the main shaft gear 44 and are able to turn, the microchips 2 have also rotated $4\alpha°$.

As shown above, when the vertically moving shaft 32 is upward, the microchips 2 are given a planetary motion as they revolve while being free to turn around the planetary main shafts 43. Therefore, this is the centrifugal direction-switching mode.

From the state shown in FIG. 13(b), when the controller again drives the direction-switching motor 30 and the eccentric cam 29 is rotated 180°, the vertically moving shaft 32 is pressed down by the eccentric cam 29 and the centrifugation mode, shown in FIG. 13(a) is achieved. If there is a change to the centrifugation mode when in the state shown in FIG. 15(b5), revolution around the main shaft 42 will occur with the microchip 2 having rotated $4\alpha°$ and centrifugal force can be made to act on the microchip 2 in the direction that follows rotation by $4\alpha°$. By operating the main shaft gear 44 by the centrifugal direction-switching mechanism 28 and changing between the centrifugation mode and the centrifugal direction-switching mode in this way, it is possible to carry out various operations with centrifugal force acting on the microchip 2 in different directions.

The case in which the rotation restricting slot 52 and the main shaft connecting pin 48 are set at opposite angles to the diametric direction of the vertically moving shaft 32 and the main shaft 42—or in other words, the case in which the rotation restricting slot 52 and the main shaft connecting pin 48 are set at 180° intervals on the arc of the vertically moving shaft 32 and the main shaft 42—is explained next. If the rotation restricting slot 52 and the main shaft connecting pin 48 are set at opposite angles to the diametric direction of the vertically moving shaft 32 and the main shaft 42, it is possible to change from the centrifugation mode to the centrifugal direction-switching mode even when in the state shown in FIG. 15(b3). If there is a change from the centrifugation mode to the centrifugal direction-switching mode when in the state shown in FIG. 15(b3), revolution around the main shaft 42 will occur with the microchip 2 having rotated $2\alpha°$ and centrifugal force can be made to act on the microchip 2 in the direction that follows rotation by $2\alpha°$.

Thus, by means of the relationship between the number of teeth on the planetary gears 34 and the number of teeth on the main shaft gear 44, and by means of the location of the rotation restricting slot 52 and the main shaft connecting pin 48, it is possible to apply centrifugal force to the microchip 2 when rotated to various angles, and to have the centrifugal force act on the microchip 2 in different directions.

Now, in the example shown here, the centrifugal direction-switching mechanism 28 raises the vertically moving shaft 32 using the eccentric cam 29, and the vertically moving shaft 32 and the main shaft gear 44 are fixed by the top engaging pin 46, but it is also possible to have a cross section of the vertically moving shaft 32 and a cross section of the main shaft gear 44 mesh and be fixed, or to have the vertically moving shaft 32 and the main shaft gear 44 fixed by a magnet or by a clutch mechanism, or to drive the main shaft 42 and the main shaft gear 44 separately and regulate their relative rates of rotation. Further, it is preferable that the vertically moving shaft 32 and the measurement chamber 19 be fixed by way of the sliding bearing 31; then, it is possible to support the main shaft 42 at both ends, to improve rigidity and to reduce vibration due to rotation of the measurement stage 23.

Having a centrifugal direction-switching mechanism 28 like this makes it possible to automatically switch the centrifugal direction applied to the microchip 2, and thus, to move the sample liquid within the microchip 2 in a complex manner. Now, the explanation given above was of a state in which a pair of microchips 2 is accommodated in the measurement stage 23, but it is also possible to examine a single microchip 2 using a simple weight on one side to counterbalance the other side. Moreover, it is possible to further increase the number of microchips 2 accommodated by the measurement stage 23.

The second embodiment of this invention is explained next, with reference to FIGS. 16 through 22. The microchip 2 of the second embodiment has a multiply formed optical measurement chamber 10, and is used for examination of multiple items.

Figure 16A:
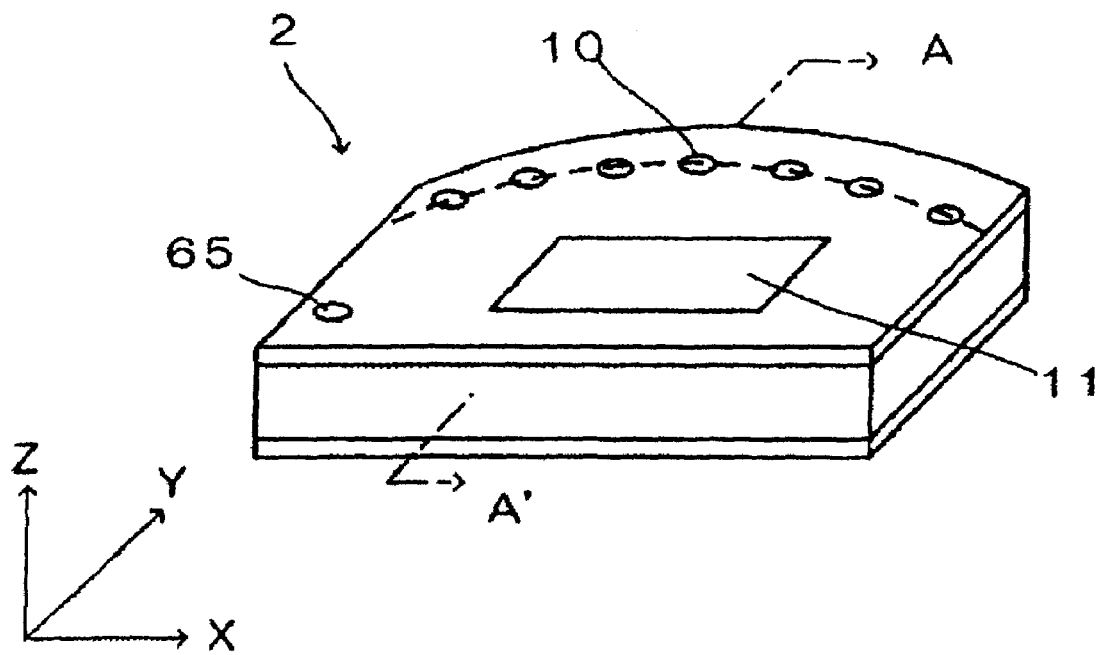
FIGS. 16(*a*) & 16(*b*) are a perspective view of the microchip and an enlarged cross-sectional view of a portion of the microchip, respectively.
Figure 16B:
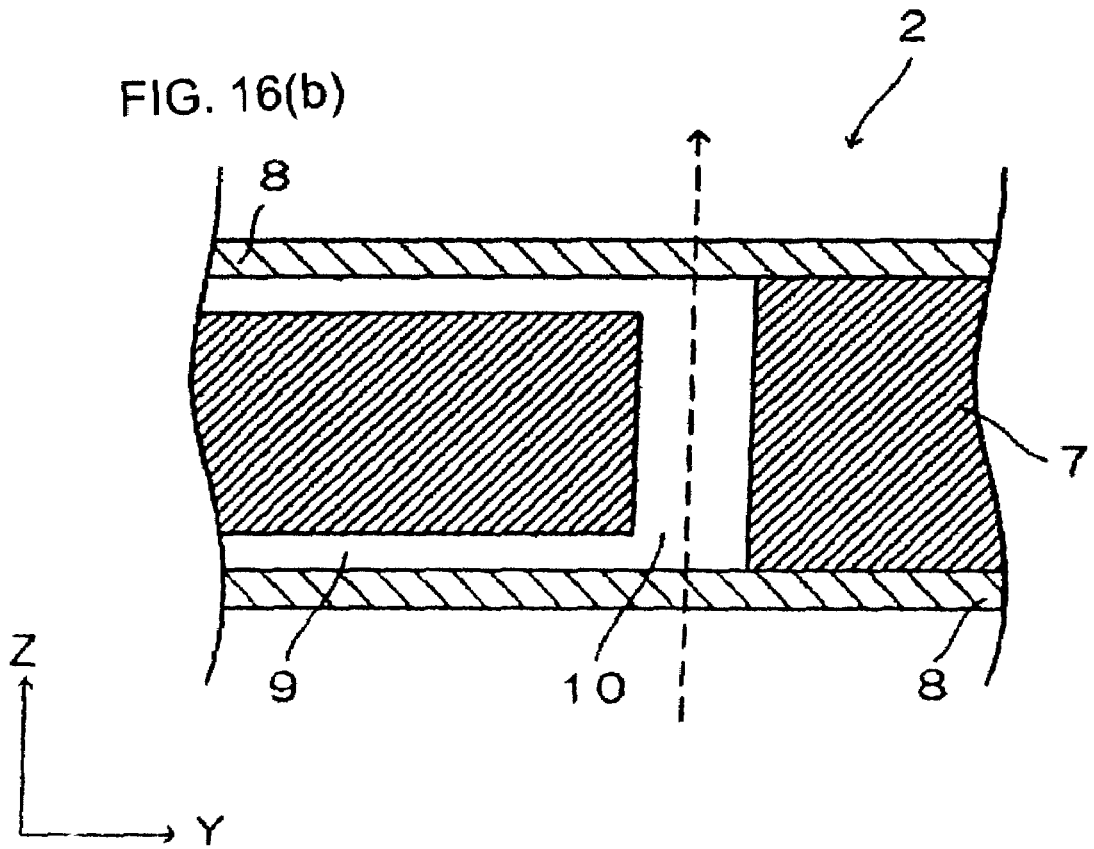

FIG. 16(a) is an external view of a microchip 2 for examination of multiple items; FIG. 16(b) is an expanded cross section taken at line A-A' of FIG. 16(a). As shown in FIG. 16(b), the microchip 2 for examination of multiple items is formed by sticking transparent resin layers 8 to the top and bottom surfaces of opaque resin layer 7. And as shown in FIG. 2(a), a fill hole 65 is formed on the upper surface of the microchip 2 for examination of multiple items, and as shown in FIG. 2(b), a groove that is the channel for the sample liquid is formed on the inside, and an optical measurement chamber 10 that is about 1.0 mm in diameter is formed. The sample liquid is introduced into the microchip 2 through the fill hole 65, at a certain stage of the examination, an unillustrated reagent or other material that has been sealed in a certain position is automatically mixed with the sample liquid to become a measurement sample liquid, and the measurement sample liquid is introduced into the optical measurement chamber 10. Analysis is performed using the absorptiometric method or another method by measuring light that is passed through the optical measurement chamber 10.

Further, a two-dimensional code 11 is attached to the front of the microchip 2; it records such information as a serial number, the effective date of the chip, the type of item measured, the position of the optical measurement chamber 10, and the reagent lot for each chip.

Figure 17:
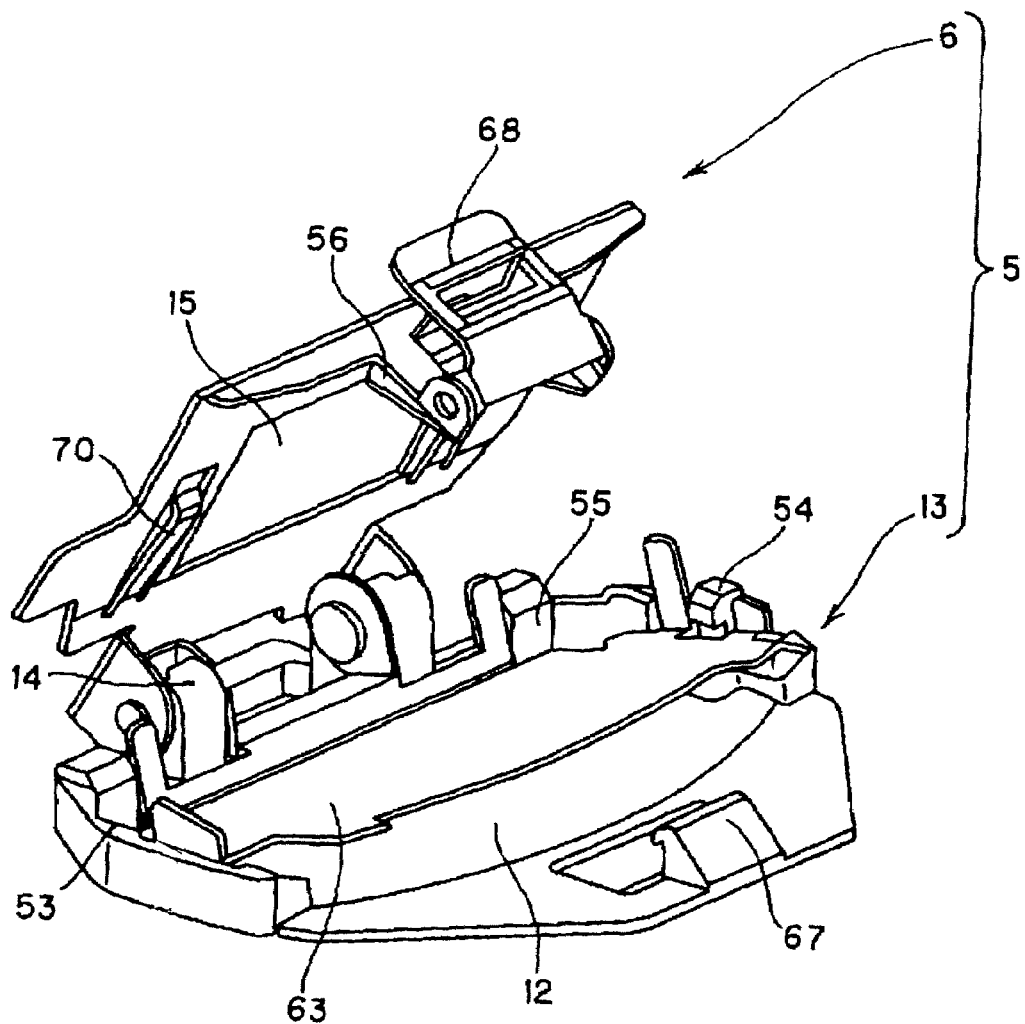
FIG. 17 is a perspective view of chip holder to be applied to microchips.
Figure 18:
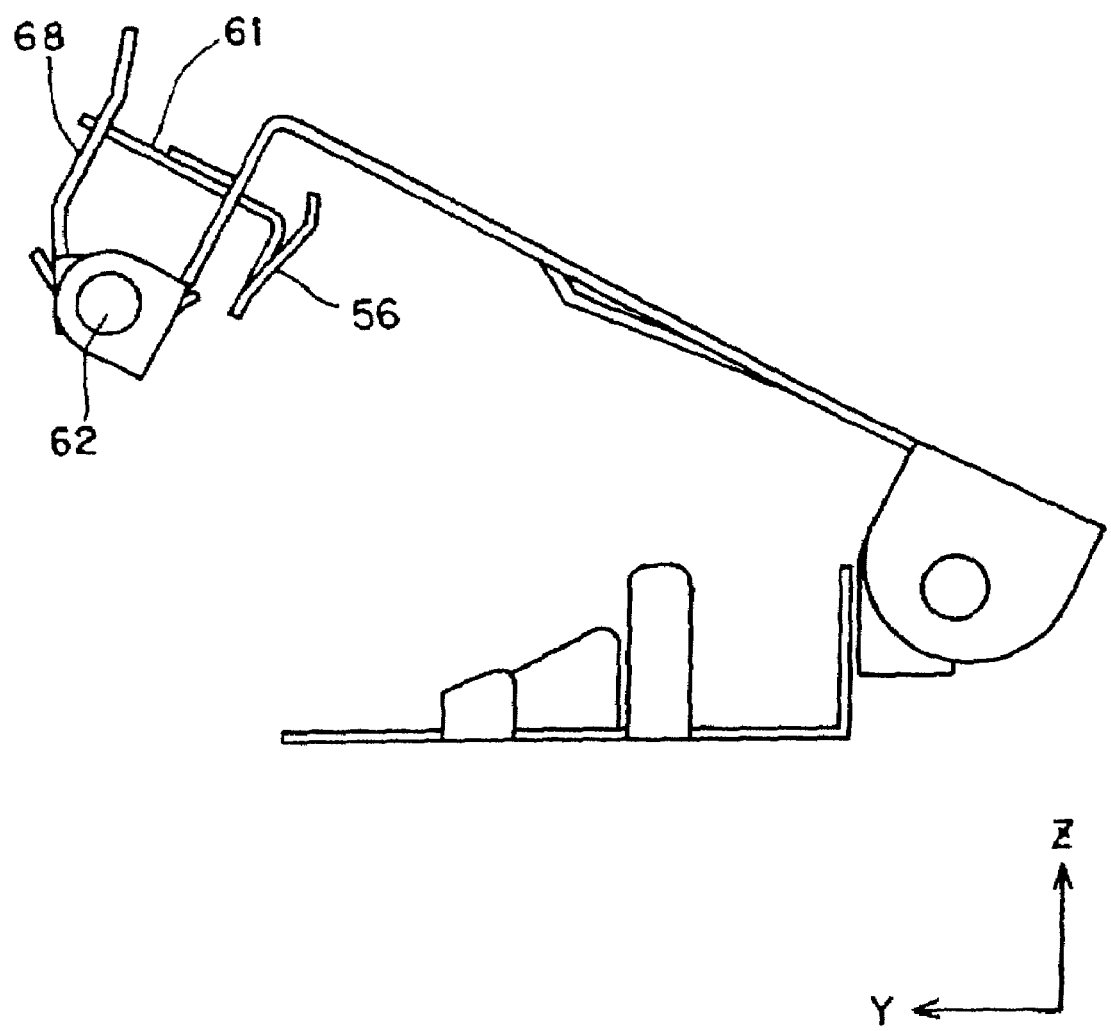
FIG. 18 a side view of the cover to be applied to microchips.

FIG. 17 is an exterior perspective view of the chip holder 5 for examination of multiple items in which the microchip 2 shown in FIG. 16 is housed.

As shown in FIG. 17, the chip holder 5 is made of a resin, for example, and comprises a box area 13 that has a chip accommodation space 12 that accommodates the microchip 2, and a metal cover 6 that positions a microchip 2 in a given location and fixes it in place. The cover 6 is fixed to fulcrums 14 by hinges, and has a code reader reading window 15 to read the two-dimensional code attached to the microchip 2 from the outside, and a sample amount sensor reading hole to examine whether the volume of the sample introduced into the microchip 2 is adequate.

So that the cover 6 will not open even when centrifugal force is applied to the microchip 2, a hook 67 on the cover 6 is slipped into a hook catch 68 in the box area 13 and fixed in place. This is because, in the event that blood is used as the sample liquid introduced into the microchip 2, it is necessary to rotate the chip at 3000 rpm for 1 minute, for example, in order to separate the blood into cells and plasma. For that reason, during revolution of the microchip 2 the centrifugal force on the chip holder 5 exceeds 400 G; the cover is fixed in place so that it will not open even under that force.

Further, the chip holder 5 has a precision tolerance error within of ±0.2 mm in the two directions perpendicular to the optical axis of the optical measurement chamber 10, and must be positioned and fixed in place so that the microchip 2 does not move within the chip accommodation space 12. The diameter of a cross section perpendicular to the optical axis of the optical measurement chamber 10, for example, 1.0 mm in diameter; that is in order to accurately measure the attenuation of the light at specific wavelengths by radiating light from the unillustrated light source precisely on the optical measurement chamber 10.

The microchip 2 must be easily accommodated in the chip holder 5 so that it can be operated by the operator without trouble. A chip supporter 63 is lifted up by a spring, for example, between the box area 13 and the cover 6 when the cover 6 is opened, and the microchip 2 can be inserted easily in the way that a cassette tape is put in and taken out. When a microchip 2 is inserted, it is enough to place the microchip 2 on the chip supporter 63, and when the microchip 2 is removed the microchip 2 lifts up from the chip accommodation space 12, and so it is easily removed.

The chip supporter 63 is formed with an extra margin for the microchip 2. For example, the length of the microchip 2 is 62 mm in the X direction and the chip supporter 63 is 63.5 mm in the Y direction, and the microchip 2 is inserted in the Y direction. The microchip 2 that is placed on the chip supporter 63 is housed in the accommodation space 12 at the same time that the cover 6 is closed.

In order to position and accommodate the microchip 2 at the same time that the cover 6 is closed, a device to position and fix the microchip 2 in the chip holder 5 is necessary. Therefore, the box area 13 of the chip holder 5 has an X reference plane 53, a Y reference plane 55, and an X direction pusher, and the cover 6 of the chip holder 5 has a Y direction pusher; the microchip 2 is positioned and fixed in place when the cover 6 is closed by engaging the hook 67 of the cover 6 in the hook catch 68.

The positioning mechanism in the X direction is explained first. The X direction pusher 54 projects from the box area 13 like a hook, and the tip that contacts the microchip 2 is machined with a tapered face. At the same time, that the cover 6 closes, the tapered face of the X direction pusher 54 guides the microchip 2 toward the X direction reference plane 53, and the X direction pusher 54 pushes the microchip 2 against the X reference plane 53. The microchip 2 is placed tightly against the X reference plane 53, and is positioned with a precision within ±0.2 mm error in the X direction.

The positioning mechanism in the Y direction is explained next. The Y direction pusher 56, because of its placement, is hard to understand from the external view of the chip holder 5 in FIG. 17, and so it is explained with reference to a diagram in which the cover 6 is seen from the X direction shown in FIG. 18.

The Y direction pusher 56 is at the tip of a projection 61 and has a face that is parallel to the Y direction reference plane 55 when the cover 6 is closed; the projection 61 is attached—by welding, for example—to the hook catch 68 of the cover 6. When the microchip 2 is fixed in place by engaging the hook 67 of the box area 13, shown in FIG. 17, in the hook catch 68 of the cover 6, the hook catch 68 moves on the hinges 62 in the direction of the Y direction reference plane 55, and the Y direction pusher 56 that is connected to the hook catch 68 also moves in the direction of the Y direction reference plane 55. By this means, at the same time that the cover 6 closes, the Y direction pusher 56 guides the microchip 2 toward the Y direction reference plane 55, and the microchip 2 pushes against the Y reference plane 55. The microchip 2 is placed tightly against the Y reference plane 55, and is positioned with a precision within ±0.2 mm error in the Y direction.

In this way, by simply placing the microchip 2 on the chip supporters 63, closing the cover 6 of the chip holder 5, and slipping the hook 67 into the hook latch 68, it is possible to position the microchip 2 in the X direction and the Y direction—the two directions perpendicular to the optical axis of the light that passes the optical measurement chamber 10.

Further, it is necessary to fix the microchip 2 in the 7 direction to some extent so that will not vibrate within the chip holder 5. When the cover 6 is closed, the Z direction pusher 70, shown in FIG. 16, fixes the microchip 2 in the Z direction. Further, so that the cover 6 does not influence the position of the microchip 2 when the cover 6 is in a closed state, a cut-out corresponding to the shape of the cover 6 is formed in the chip accommodation space 12 so that the cover 6 does not put pressure on the microchip 2.

Figure 19:
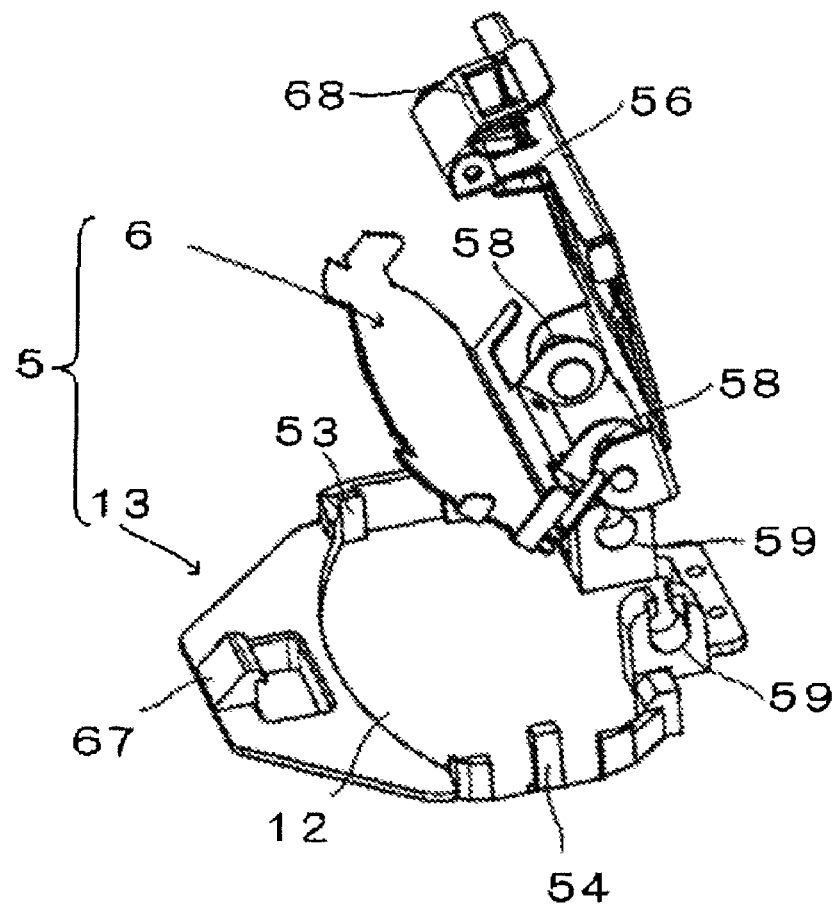
FIGS. 19(*a*) & 19(*b*) are a perspective view of chip holder to be applied to microchips and sectional views for explaining how the cover of the chip holder is detachable.
Figure 19:
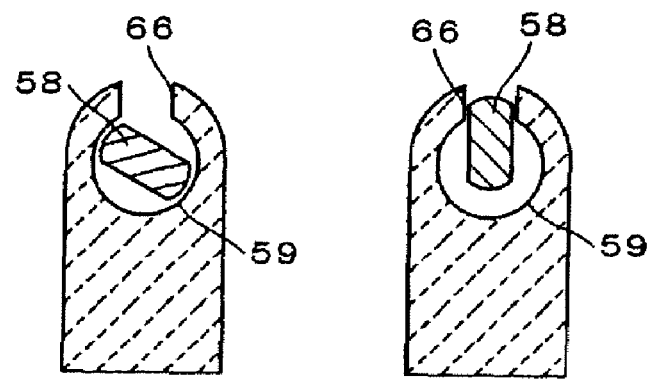

FIG. 19(*a*) is a diagram to explain that the cover 6 of the chip holder 5 is detachable; FIG. 19(*b*) is an expanded cross section of the attachment of a fulcrum 14 and the cover 6.

The convex area 59 of the fulcrum 14 is a bearing with an opening at the top. If the opening has the same width as the maximum diameter of the bearing, it would be possible to put in and take out a spindle that was circular in cross section. The convex area 58 of the cover 6 fits into the concave area 59 and functions as the pivot of the fulcrum 14. However, a concave area 58 that was circular in cross section would be easy to put in and take out, but the concave area 58 would not stay in.

FIG. 19(*b*) is a cross section of the attachment of the concave area 59 having a narrow opening 66 and a convex area 58 that is roughly rectangular in cross section.

So that the convex area 58 does not disengage, a narrow opening 66 is formed as a part of a keyhole-shaped concave area 59, and a convex area 58 that is roughly rectangular in cross section, with the two sides of the circular cross section cut away, is formed to correspond to the keyhole shaped concave area 59 so that it can enter the opening 66. If the convex area 58 that is roughly rectangular in cross section is made to fit into the concave area 59 with its narrow opening 66, the convex area 58 will engage in the concave area 59 and not disengage during the operations of accommodating the microchip 2 in the chip holder 5 or removing it therefrom. However, if the operator opens the cover 6 widely so that it is perpendicular to the box area 13, the convex area 58 that is roughly rectangular in cross section will align with the opening 66 of the concave area 59, and if the cover 6 is pulled upward in that state, it can be removed simply, without the use of auxiliary tools. If there are, for example, leaf springs at points where the cover 6 and the box area 13 are in contact, so that there is always an upward force on the cover 6, simply aligning the convex area 58 that is roughly rectangular in cross section with the opening 66 of the concave area 59 will automatically release the cover 13. The cover 6 can be re-attached to the box area 13 by reversing this process.

In this way, the cover 6 and the box area 13 of the chip holder 5 have a concave area 59 and a convex area 58, and because of the fitted relationship of the concave area 59 and the convex area 58, it is possible to separate or attach the cover 6 and the box area 13 by simply opening the cover 6 widely or aligning the shape of the convex area 58 to the opening 66 of the concave area 59, and so the cover 6 can be removed from the microchip testing device and washed simply, without using auxiliary tools such as screwdrivers or wrenches.

Figure 20:
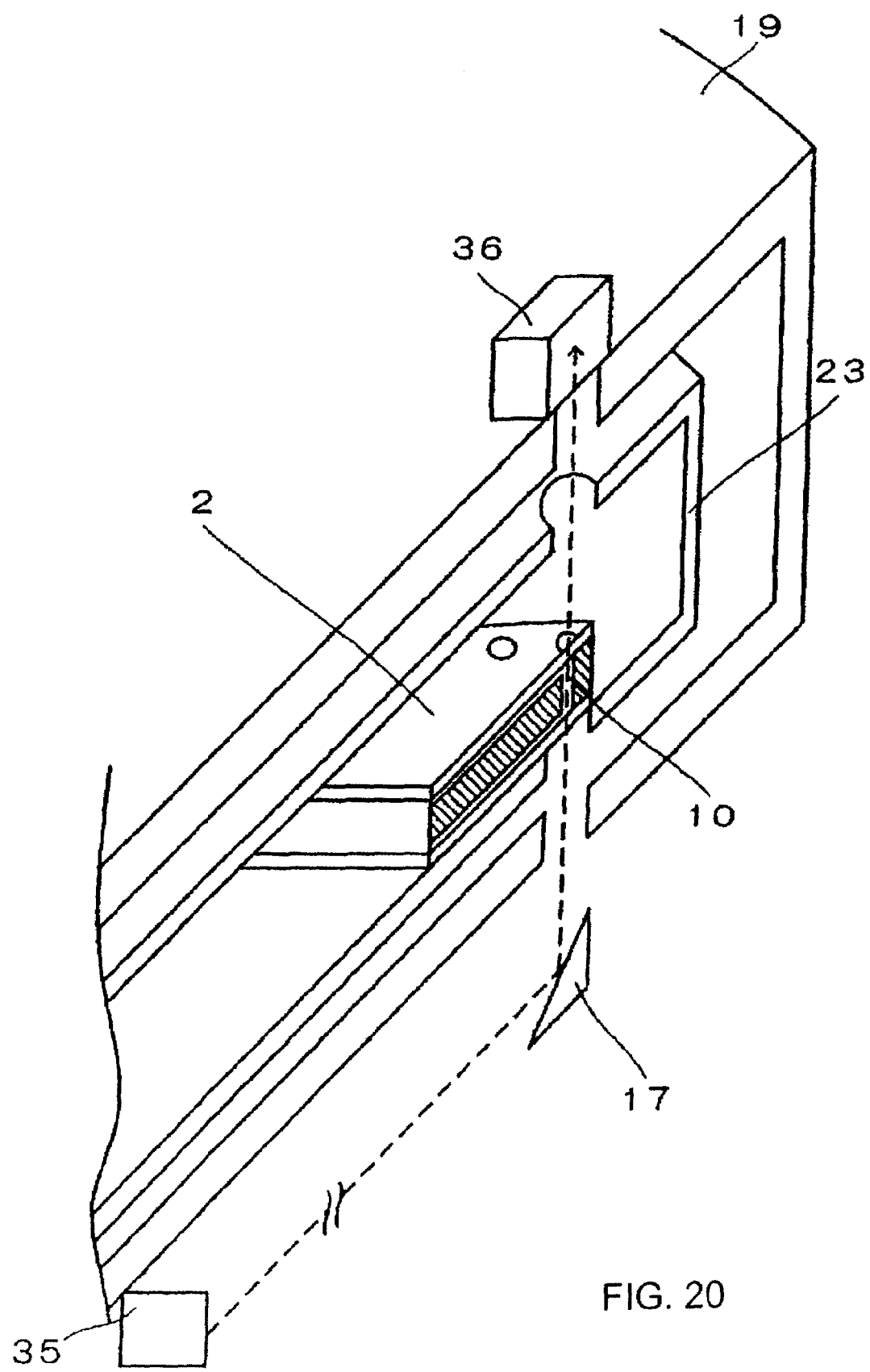
FIG. 20 is a perspective cross-sectional view showing an example of the layout of the light source and detector in the microchip testing device to be applied to microchips.

FIG. 20 is a partial cross section that shows the layout of the light source 35 and the detector 36 in microchip testing device that is suited to the microchip 2 shown in FIG. 16(*a*).

As shown in FIG. 20, light emitted by the light source 35 is, for example, converted to parallel light by a lens or other means; the parallel light is reflected by a mirror 17 and passes the optical measurement chamber 10 of the microchip 2 to which it is perpendicular. The transiting light is received by a detector 36. By placing the light source 35 and the detector 36 in this way, it is possible to perform analysis by means of the absorptiometric method or other methods in a microchip testing device that uses a microchip 2 for examination of a single item by switching to a chip holder 5 that accommodates a microchip 2 for examination of multiple items.

Figure 21:
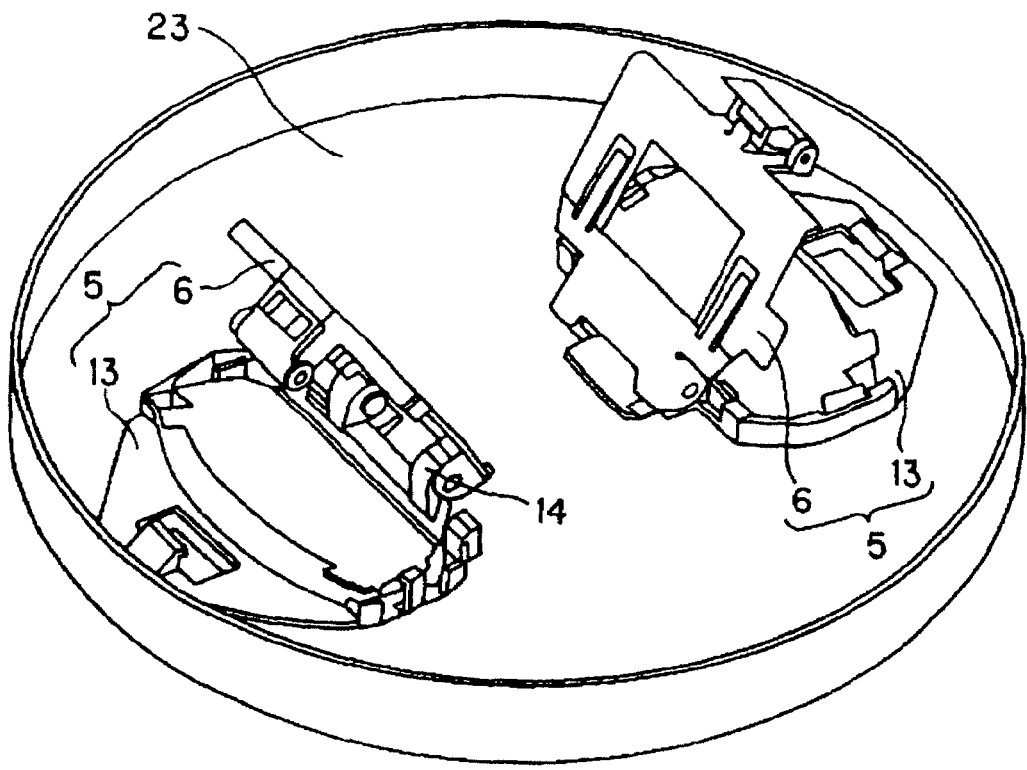
FIG. 21 is a perspective view showing the internal structure of the measurement chamber.

FIG. 21 is a perspective view of the measurement stage 23 in which are installed microchips 2 for examination of multiple items.

The microchips 2 are housed in chip holders 5 that are placed symmetrically relative to the center of the measurement stage 23. The box areas 13 of the chip holder 5 are formed as a unit with the measurement stage 23, and the cover 6 is fixed by hinges to fulcrums 14 that project from the measurement stage 23. The measurement stage 23 is rotated counter-clockwise by a rotary drive source such as drive source 39 described above.

Figure 22:
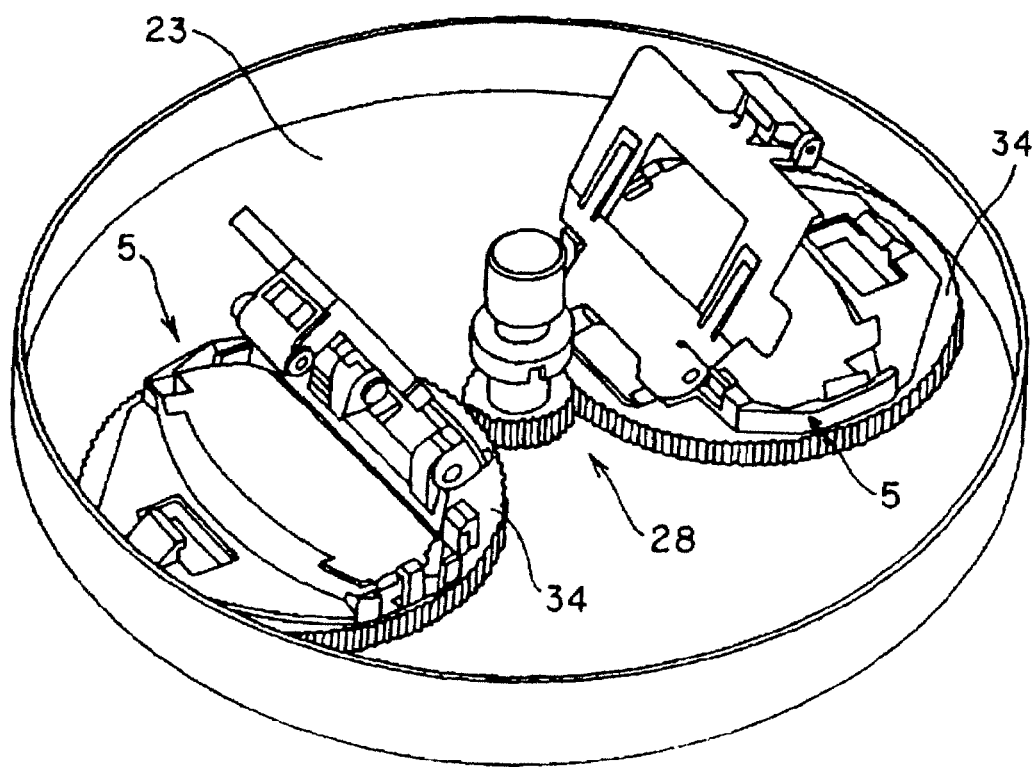
FIG. 22 is a perspective view showing the internal structure of the measurement chamber with a centrifugal direction-switching mechanism.
Figure 23:
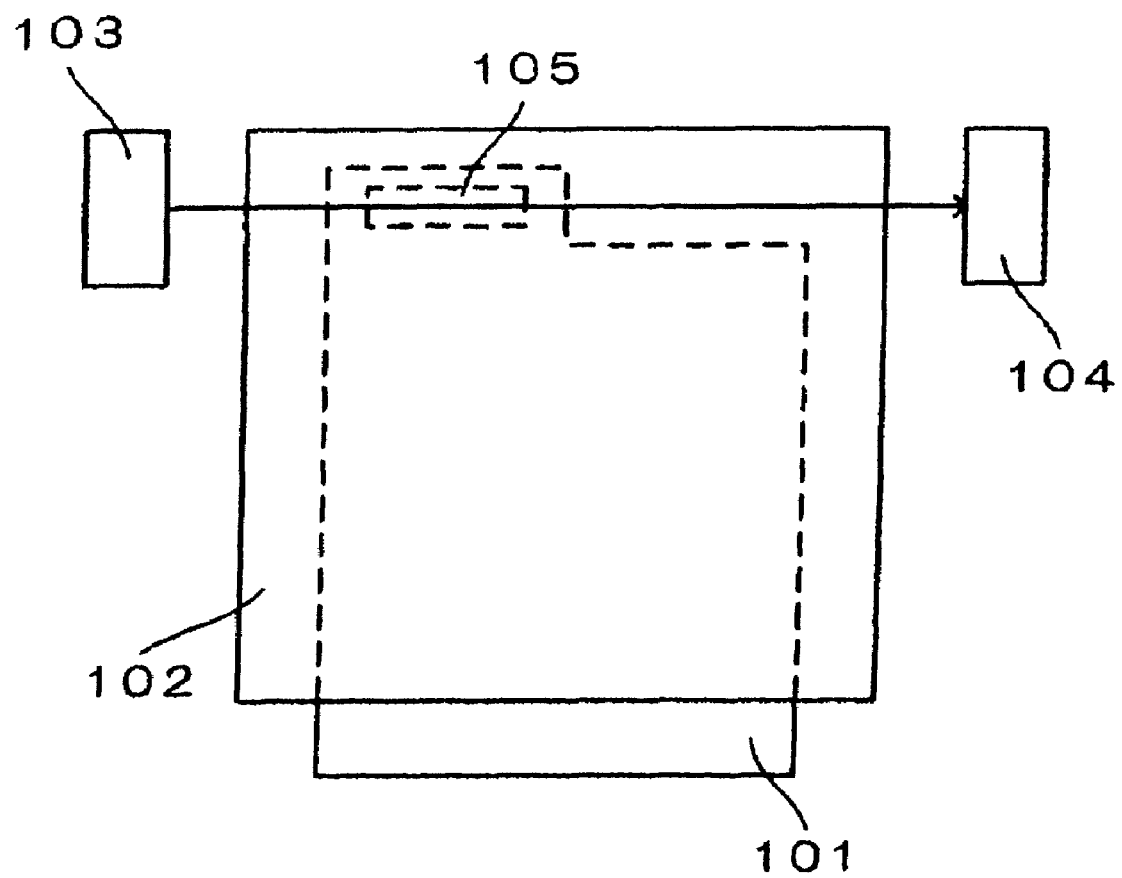
FIG. 23 is a diagram of an example of conventional centrifugation equipment used for blood analysis.

FIG. 22 is a perspective view of a measurement stage 23 to which a centrifugal direction-switching mechanism 28 is attached.

The centrifugal direction-switching mechanism 28 is attached to the center of the measurement stage 23 and the microchips 2 are housed in chip holders 5 that are placed symmetrically on the centrifugal direction-switching mechanism 28. The chip holders 5 are placed on planetary gears 34 that have teeth formed on their sides. Now, the structure of the measurement chamber 19, the centrifugal direction-switching mechanism 28, and so on correspond to that in the first embodiment, and the microchip testing device can be operated by replacing the measurement stage 23 with microchips 2 for examination of single items installed with a measurement stage 23 with microchips 2 for examination of multiple items installed.

In this way, the box area 13 has an X reference plane 53 and a Y reference plane 55 that position the microchip 2 in two directions perpendicular to the optical axis of the optical measurement chamber 10 in the chip holder 5, there is an X direction pusher 54 and a Y direction pusher 55 that push the microchip 2 against the respective reference planes, and the microchip 2 is positioned within the chip holder 5 by closing the cover 6 of the chip holder 5. By this means, the microchip 2 can be positioned in two directions perpendicular to the optical axis of the optical measurement chamber 10, and so it is possible to accurately radiate light from the light source 35 into the optical measurement chamber 10, to receive light that has passed the optical measurement chamber 10, and to calculate analysis results on the basis of the amount of light received.

What is claimed is:

1. Microchip testing device, comprising:
 a measurement stage,
 a chip holder having a cover and a box area that are connected together by a hinge and which is mounted on the measurement stage,
 a microchip that has an optical measurement chamber and is housed in the chip holder,
 a light source that radiates light on the optical measurement chamber of the microchip,
 a detector that receives light that has passed through the optical measurement chamber, and
 a controller that controls the device,
 wherein the chip holder has X and Y direction reference planes to position the microchip in X and Y directions perpendicular to an optical axis of the optical measurement chamber and X and Y direction pushers that push the microchip against the X and Y direction reference planes, respectively, and
 wherein at least the Y direction pusher pushes the microchip in the Y direction and the microchip pushes against the Y direction reference plane so that the microchip is positioned within the chip holder in at least the Y direction by closing the cover of the chip holder.

2. Microchip testing device as described in claim 1, wherein a surface of at least one of the pushers is a tapering bevel.

3. Microchip testing device as described in claim 1, wherein one of the pushers comprises an element on the cover and an element on the box area, and wherein one of said elements has a tapering bevel.

4. Microchip testing device as described in claim 1, wherein the hinge connecting the cover and box area of the chip holder is formed by concave and convex areas that have an interlocking relationship by which the cover and box area are engaged and separated.

5. Microchip testing device as described in claim 2, wherein one of the pushers comprises an element on the cover and an element on the box area, and wherein one of said elements has a tapering bevel.

* * * * *